(12) United States Patent
Xia et al.

(10) Patent No.: US 9,439,897 B2
(45) Date of Patent: Sep. 13, 2016

(54) USE OF PSORALEN DERIVATIVES AND COMBINATION THERAPY FOR TREATMENT OF CELL PROLIFERATION DISORDERS

(71) Applicants: IMMUNOLIGHT, LLC, Detroit, MI (US); DUKE UNIVERSITY, Durham, NC (US)

(72) Inventors: Wenle Xia, Durham, NC (US); David Gooden, Durham, NC (US); Erik J. Soderblom, Durham, NC (US); Eric J. Toone, Durham, NC (US); Neil L. Spector, Durham, NC (US); Wayne F. Beyer, Jr., Belville, NC (US); Harold Walder, Belville, NC (US)

(73) Assignees: IMMUNOLIGHT, LLC, Detroit, MI (US); DUKE UNIVERSITY, Durham, NC (US)

( * ) Notice: Subject to any disclaimer, the term of this patent is extended or adjusted under 35 U.S.C. 154(b) by 0 days.

(21) Appl. No.: 14/603,539

(22) Filed: Jan. 23, 2015

(65) Prior Publication Data

US 2015/0202294 A1 Jul. 23, 2015

Related U.S. Application Data

(60) Provisional application No. 61/930,717, filed on Jan. 23, 2014.

(51) Int. Cl.
| | | |
|---|---|---|
| *A61K 31/517* | (2006.01) | |
| *A61K 31/4709* | (2006.01) | |
| *A61K 31/436* | (2006.01) | |
| *A61K 31/37* | (2006.01) | |
| *A61K 41/00* | (2006.01) | |

(52) U.S. Cl.
CPC ............ *A61K 31/4709* (2013.01); *A61K 31/37* (2013.01); *A61K 31/436* (2013.01); *A61K 31/517* (2013.01); *A61K 41/0066* (2013.01)

(58) Field of Classification Search
None
See application file for complete search history.

(56) References Cited

U.S. PATENT DOCUMENTS

| | | | |
|---|---|---|---|
| 4,748,120 A | 5/1988 | Wiesehahn | |
| 4,838,852 A | 6/1989 | Edelson et al. | |
| 4,979,935 A | 12/1990 | Lindmayer | |
| 5,216,176 A | 6/1993 | Heindel et al. | |
| 5,556,612 A | 9/1996 | Anderson et al. | |
| 5,829,448 A | 11/1998 | Fisher et al. | |
| 5,980,054 A | 11/1999 | Fukui et al. | |
| 5,984,887 A | 11/1999 | McLaughlin et al. | |
| 6,204,058 B1 | 3/2001 | Bolton | |
| 6,235,508 B1 | 5/2001 | Sowemimo-Coker et al. | |
| 6,569,467 B1 | 5/2003 | Bolton | |
| 6,669,965 B2 | 12/2003 | Bolton | |
| 6,849,058 B1 | 2/2005 | Levy et al. | |
| 6,908,591 B2 | 6/2005 | MacPhee et al. | |
| 7,045,125 B2 | 5/2006 | Erbe et al. | |
| 2002/0127224 A1 | 9/2002 | Chen | |
| 2009/0148402 A1 | 6/2009 | Brunetta et al. | |
| 2010/0113474 A1 | 5/2010 | Zacharhuk et al. | |
| 2011/0111018 A1 | 5/2011 | Ashraf et al. | |
| 2013/0131429 A1 | 5/2013 | Toone et al. | |

FOREIGN PATENT DOCUMENTS

WO    WO 03/049801    6/2003

OTHER PUBLICATIONS

International Search Report and Written Opinion of the International Searching Authority issued May 19, 2015 in PCT/US2015/012669 (with Search History).
Aertgeerts et al, "Structural Analysis of the Mechanism of Inhibition and Allosteric Activation of the Kinase Domain of HER2 Protein", (2011). J Biol Chem 286: 18756-18765.
Anido et al. "Biosynthesis of tumorigenic HER2 C-terminal fragments by alternative initiation of translation" (2006) EMBO J 25: 3234-3244.
Berger et al, "Comparison of synthetic psoralen derivatives and 8-MOP in the inhibition of lymphocyte proliferation", (1985). Ann N Y Acad Sci 453: 80-90.
Canton et al, "PUVA-induced apoptosis involves mitochondrial dysfunction caused by the opening of the permeability transition pore," (2002) FEBS Letters 522: 168-172.
Cimino et al, "Psoralens as photoactive probes of nucleic acid structure and function: organic chemistry, photochemistry, and biochemistry," (1985) Annu Rev Biochem 54: 1151-1193.
Di Cosimo et al "Management of breast cancer with targeted agents: importance of heterogeneity", (2010) Nat Rev Clin Oncol 7: 139-147.
Edelson et al, "Treatment of cutaneous Tcell lymphoma by extracorporeal photochemotherapy. Preliminary results". (1987) N Engl J Med 316: 297-303.
Geyer et al, "Lapatinib plus capecitabine for HER2-positive advanced breast cancer," (2006) N Engl J Med 355: 2733-2743.
Grenix et al, "Successful use of extracorporeal photochemotherapy in the treatment of severe acute and chronic graft-versus-host disease", (1998) Blood 92: 3098-3104.
Hearst et al, "The reaction of the psoralens with deoxyribonucleic acid," (1984) Q Rev Biophys 17:1-44.
Johnston et al "Targeting HER2 in advanced inflammatory breast cancer with lapatinib monotherapy: A phase II study with biomarker profiles that predict for response", (2008) J Clin Oncol 26: 1066-1072.
Laskin et al, "A possible mechanism of psoralen phototoxicity not involving direct interaction with DNA", (1985) Proc Natl Acad Sci US. 82: 6158-6162.
Liang et al, "Sensitization of breast cancer cells to radiation by trastuzumab", (2003) Mol Cancer Ther 2: 1113-1120.

(Continued)

*Primary Examiner* — Heidi Reese
(74) *Attorney, Agent, or Firm* — Oblon, Spivak, McClelland, Maier & Neustadt, L.L.P.

(57) ABSTRACT

Methods for the treatment of a cell proliferation disease or disorder in a subject, involving applying a psoralen derivative lacking a DNA cross-linking motif to cancer cells, applying a psoralen or a derivative thereof and lapatinib, or applying a psoralen or derivative thereof and neratinib, to a subject and further applying initiation radiation energy form an energy source.

29 Claims, 7 Drawing Sheets
(7 of 7 Drawing Sheet(s) Filed in Color)

(56) References Cited

OTHER PUBLICATIONS

Mermelstein et al, "Inhibition of epidermal growth factor receptor tyrosine kinase activity in A431 human epidermoid cells following psoralen/ultraviolet light treatment", (1989) Mol Pharmacology 36: 848-855.

Nahta et al, "Mechanisms of disease: understanding resistance to HER2-targeted therapy in human breast cancer", (2006) Nat Clin Pract Oncol 3: 269-280.

Parrish et al, "Photochemotherapy of psoriasis with oral methoxsalen and longwave ultraviolet light", (1974) N Engl J Med 291: 1207-1211.

Polier et al, "ATP-competitive inhibitors block protein kinase recruitment to the Hsp90-Cdc37 system", (2013) Nat Chem Biol 9: 307-312.

Rabindran et al, "Antitumor activity of HKI-272, an orally active, irreversible inhibitor of the HER-2 tyrosine kinase", (2004) Cancer Res 264: 3958-3965.

Slamon et al, J, "Human breast cancer: correlation of relapse and survival with amplification of the HER-2/neu oncogene", (1987) Science 235: 177-182.

Slamon et al, "Studies of the HER-2/neu proto-oncogene in human breast and ovarian cancer", (1989) Science 244: 707-712.

Xia et al, "An heregulin- EGFR-HER3 autocrine signaling axis can mediate acquired lapatinib resistance in HER2+ breast cancer models", (2013) Breast Cancer Res 15: R85.

Xia et al, "A model of acquired autoresistance to ErbB2 tyrosine kinase inhibitors and a therapeutic strategy to prevent its onset in breast cancer", (2006) Proc Natl Acad Sci USA 103: 7795-7800.

Xia et al, "Combining lapatinib (GW572016), a small molecule inhibitor of ErbB1 and ErbB2 tyrosine kinases, with therapeutic anti-ErbB2 antibodies enhances apoptosis of ErbB2 overexpressing breast cancer cells", (2005) Oncogene 24: 6213-6221.

Xia et al, "Truncated ErbB2 Expressed in Tumor Cell Nuclei Contributes to Acquired Therapeutic Resistance to ErbB2 Kinase Inhibitors", (2011) Mol Cancer Ther 10: 1367-1374.

Toyooka et al, "Histone Deacetylase Inhibitor Sodium Butyrate Enhances the Cell Killing Effect of Psoralen plus UVA by Attenuating Nucleotide Excision Repair", (2009). Cancer Res 69: 3492-3500.

Munshi et al, "Histone Deacetylase Inhibitors Radiosensitize Human Melanoma Cells by Suppressing DNA Repair Activity", (2005) Clin. Cancer Res 11: 4912-4922.

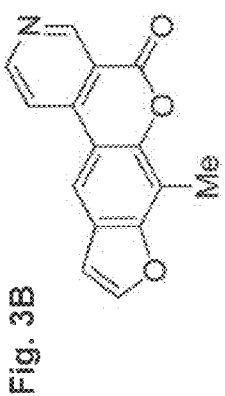
Fig. 3A
8MOP
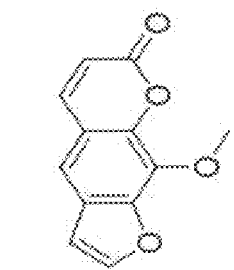
Fig. 3B
7-methylpyridopsoralen (SMSF032310)
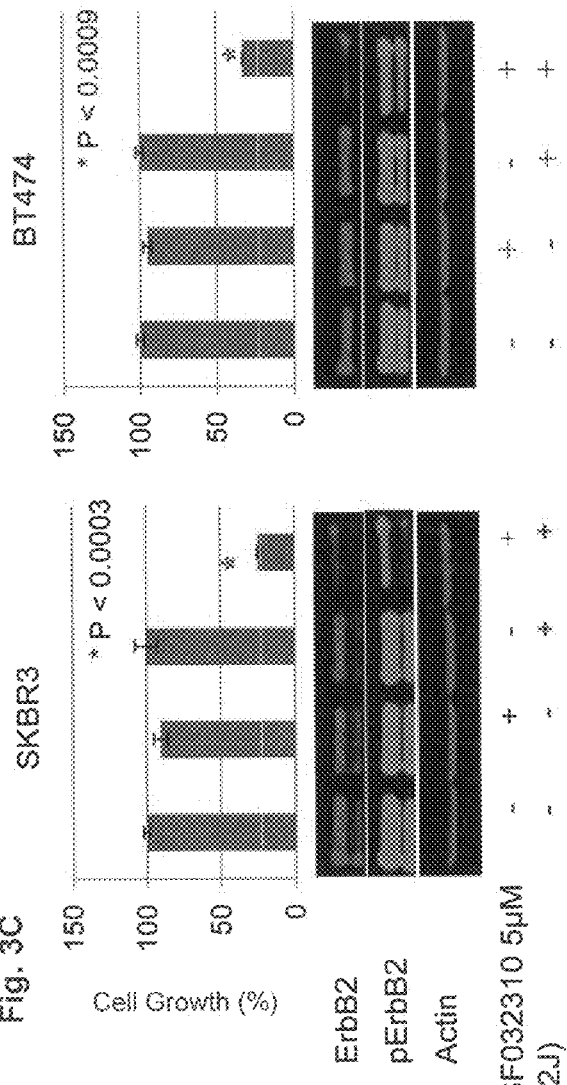
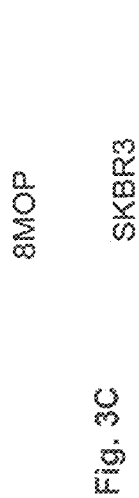
Fig. 3C

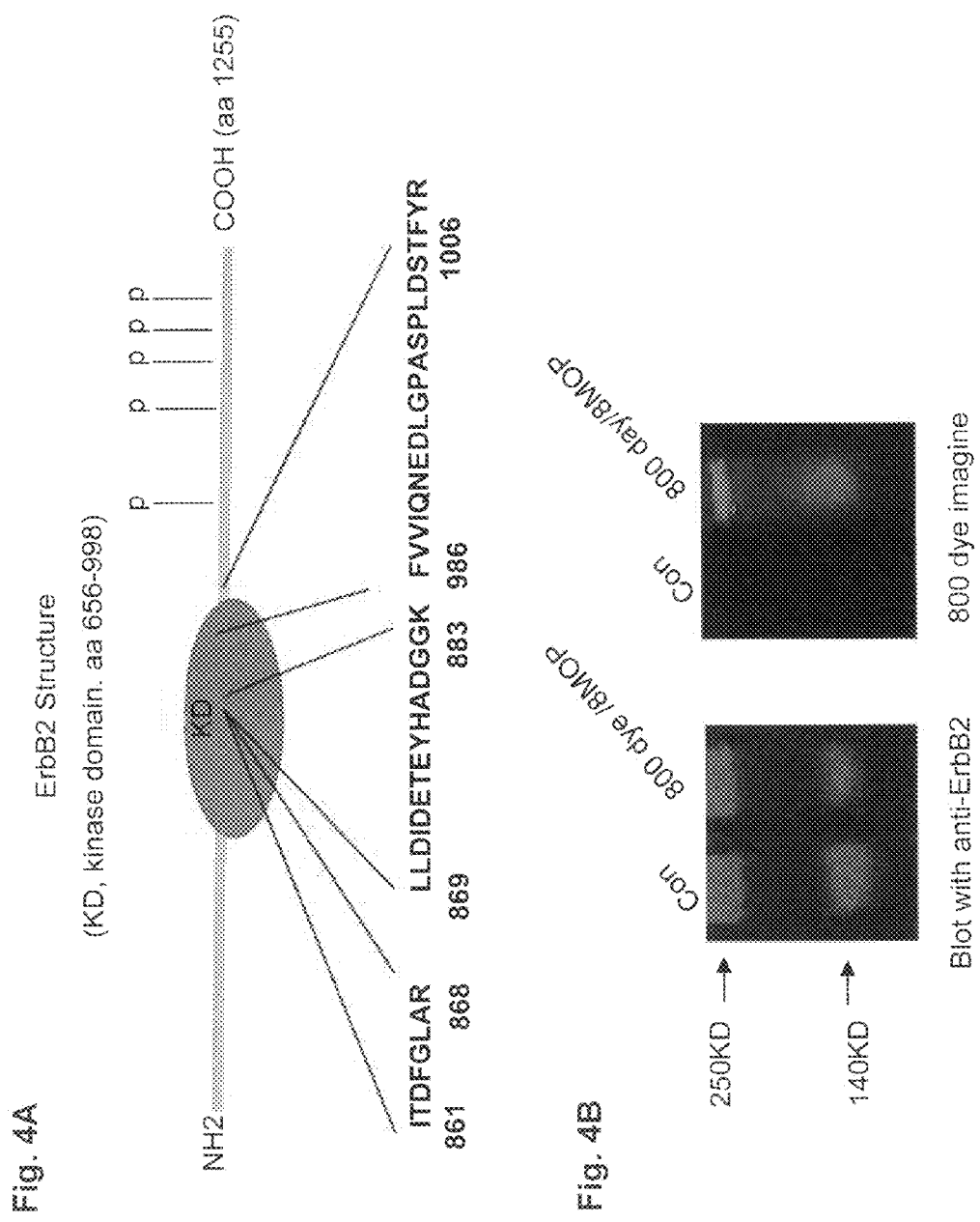

(* p < 0.0060,  p < 0.0011, * p < 0.0002)

USE OF PSORALEN DERIVATIVES AND COMBINATION THERAPY FOR TREATMENT OF CELL PROLIFERATION DISORDERS

CROSS REFERENCE TO RELATED APPLICATIONS

This application claims priority to U.S. Provisional Application No. 61/930,717, filed Jan. 23, 2014, the disclosure of which is incorporated herein by reference in its entirety.

This application is related to U.S. application Ser. No. 11/935,655, filed Nov. 6, 2007; Ser. No. 12/389,946, filed Feb. 20, 2009; Ser. No. 12/401,478, filed Mar. 10, 2009; Ser. No. 12/417,779, filed Apr. 3, 2009; Ser. No. 12/764,184, filed Apr. 21, 2010; Ser. No. 12/843,188, filed Jul. 26, 2010; Ser. No. 13/054,279, which is a national stage application of PCT/US2009/050514, filed Jul. 14, 2009, Ser. No. 13/739,398, filed Jan. 11, 2013; and Ser. No. 13/739,414, filed Jan. 11, 2013, and to U.S. Pat. No. 8,389,958, issued Mar. 5, 2012, and U.S. Pat. No. 8,383,836, issued Feb. 26, 2013, the contents of which are hereby incorporated herein by reference.

BACKGROUND OF THE INVENTION

1. Field of Invention

The present invention relates to methods for treating cell proliferation disorders involving applying a psoralen derivative lacking a DNA cross-linking motif to cancer cells, a psoralen or a derivative thereof and lapatinib, or a psoralen or derivative thereof and neratinib, to a subject and applying initiation radiation energy from an energy source.

2. Discussion of the Background

Cell Proliferation Disorders

There are several types of cell proliferation disorders. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Of these, cancer is perhaps the most well known. The term "cancer" generally refers to a diverse class of diseases that are commonly characterized by an abnormal proliferation of the diseased cells. A unifying thread in all known types of cancer is the acquisition of abnormalities in the genetic material of the cancer cell and its progeny. Once a cell becomes cancerous, it will proliferate without respect to normal limits, invading and destroying adjacent tissues, and may even spread to distant anatomic sites through a process called metastasis. These life-threatening, malignant properties of cancers differentiate them from benign tumors, which are self-limited in their growth and do not invade or metastasize.

The impact of cancer on society cannot be overstated. The disease may affect people at all ages, with a risk factor that significantly increases with a person's age. It has been one of the principal causes of death in developed countries and, as our population continues to age, it is expected to be an even greater threat to our society and economy. Therefore, finding cures and effective treatments for cancer has been, and remains, a priority within the biomedical research community.

Psoralens and Related Compounds

U.S. Pat. No. 6,235,508 further teaches that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The cross-linking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

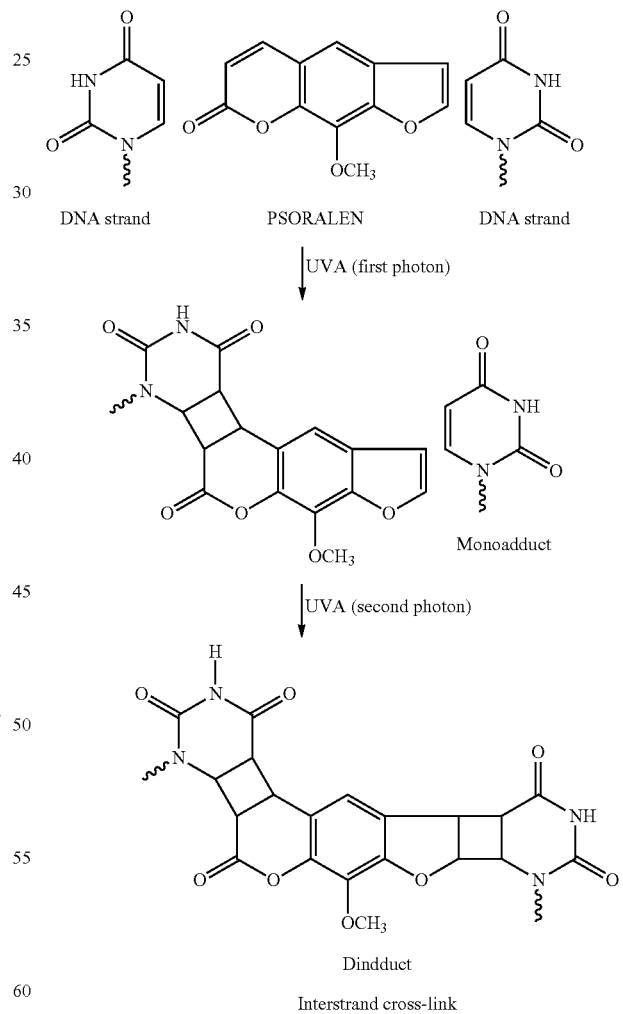

In addition, the reference teaches that 8-MOP is unsuitable for use as an antiviral, because it damages both cells and viruses. Lethal damage to a cell or virus occurs when the psoralen is intercalated into a nucleic acid duplex in sites containing two thymines (or uracils) on opposing strands but only when it sequentially absorbs 2 UVA photons and thymines (or uracils) are present. U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens. Regardless, it is believed that no auto vaccine effect has been observed.

The best known photoactivatable compounds are derivatives of psoralen or coumarin, which are nucleic acid intercalators. The use of psoralen and coumarin photo sensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species, such as shown below for coumarin:

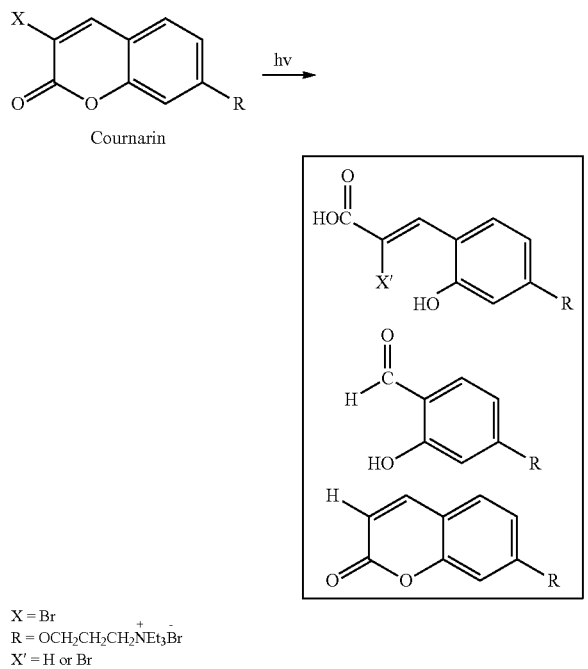

X = Br
R = OCH$_2$CH$_2$CH$_2$NEt$_3^+$Br$^-$
X' = H or Br

Research in this field over-simplifies mechanisms involved in the photoactivating mechanism and formation of highly reactive oxygen species, such as singlet oxygen. Both may lead to inactivating damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photophoresis causes the activation of an immune response with cytotoxic effects on untreated malignant cells. While the complexity of the immune response and cytotoxid effects is fully appreciated by researchers, a therapy that harnesses the system to successfully stimulate an auto vaccine effect against a targeted, malignant cell has been elusive, except for extracorporeal photophoresis for treating lymphoma.

Midden (W. R. Midden, Psoralen DNA photobiology, Vol II (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. U.S. Pat. No. 6,235,508 teaches that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 of Heindel discloses a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference.

U.S. Pat. No. 5,984,887 discloses using extracorporeal photophoresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Treatment Methods

Existing treatments for cell proliferation disorders such as cancer include surgery, chemotherapy, radiation therapy, immunotherapy, monoclonal antibody therapy, and several other lesser known methods. The choice of therapy usually depends on the location and severity of the disorder, the stage of the disease, as well as the patient's response to the treatment.

While some treatments may only seek to manage and alleviate symptoms of the disorder, the ultimate goal of any effective therapy is the complete removal or cure of all disordered cells without damage to the rest of the body. With cancer, although surgery may sometimes accomplish this goal, the propensity of cancer cells to invade adjacent tissue or to spread to distant sites by microscopic metastasis often limits the effectiveness of this option. Similarly, the effectiveness of current chemotherapy is often limited by toxicity to other tissues in the body. Radiation therapy suffers from similar shortcomings as other aforementioned treatment methods. Most of these cancer treatment methods, including radiation therapy, are known to cause damage to DNA, which if not repaired during a critical stage in mitosis, the splitting of the cell during cell proliferation, leads to a programmed cell death, i.e. apoptosis. Further, radiation tends to damage healthy cells, as well as malignant tumor cells.

A number of patents describe ex vivo treatment of bodily fluids, for example blood. Blood is obtained from a patient, treated with a photosensitive agent, exposed to UV radiation, and reinjected to the patient (i.e. extracorporeal photopheresis). Alternatively, a patient can be treated in vivo with a photosensitive agent followed by the withdrawal of a sample from the patient, treatment with UV radiation in vitro (ex vivo), and reinjecting the patient with the treated sample. This method is known for producing an autovaccine. A method of treating a patient with a photosensitive agent, exposing the patient to an energy source and generating an autovaccine effect wherein all steps are conducted in vivo has not been described. See WO 03/049801, U.S. Pat. No. 6,569,467; U.S. Pat. No. 6,204,058; U.S. Pat. No. 5,980,954; U.S. Pat. No. 6,669,965; U.S. Pat. No. 4,838,852; U.S. Pat. No. 7,045,124, and U.S. Pat. No. 6,849,058. Moreover, the side effects of extracorporeal photopheresis are well known and include nausea, vomiting, cutaneous erythema, hypersensitivity to sunlight, and secondary hematologic malignancy. Researchers are attempting to use photopheresis in experimental treatments for patients with cardiac, pulmonary and renal allograft rejection; autoimmune diseases, and ulcerative colitis.

A survey of known treatment methods reveals that these methods tend to face a primary difficulty of differentiating between normal cells and target cells when delivering treatment, often due to the production of singlet oxygen which is known to be non-selective in its attack of cells, as well as the need to perform the processes ex vivo, or through highly invasive procedures, such as surgical procedures in order to reach tissues more than a few centimeters deep within the subject.

U.S. Pat. No. 5,829,448 describes simultaneous two photon excitation of photo-agents using irradiation with low energy photons such as infrared or near infrared light (NRI). A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest.

Chen et al., J. Nanosci. and Nanotech., 6:1159-1166 (2006); Kim et al., JACS, 129:2669-2675 (2007); U.S. 2002/0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 discloses methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multicellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue. However, the method is not suitable for treating a patient and does not teach any mechanisms for stimulating the photosensitizers, indirectly.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photosensitizer, inactivating substantially all of the contaminants in the blood, without destroying the red blood cells. The blocking agent prevents or reduces deleterious side reactions of the photo sensitizer, which would occur if not in the presence of the blocking agent. The mode of action of the blocking agent is not predominantly in the quenching of any reactive oxygen species, according to the reference.

Also, U.S. Pat. No. 6,235,508 suggests that halogenated photosensitizers and blocking agents might be suitable for replacing 8-methoxypsoralen (8-MOP) in photophoresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photophoresis for antiviral treatments of raw blood and plasma.

U.S. Pat. No. 6,235,508 teaches away from 8-MOP and 4'-aminomethyl-4,5',8-trimethylpsoralen (AMT) and many other photoactivatable molecules, which are taught to have certain disadvantages. Fluorescing photosensitizers are said to be preferred, but the reference does not teach how to select a system of fluorescent stimulation or photoactivation using fluorescent photosensitizers. Instead, the fluorescing photosensitizer is limited to the intercalator that is binding to the DNA. The reference suggests that fluorescence indicates that such an intercalator is less likely to stimulate oxygen radicals. Thus, the reference fails to disclose any mechanism of photoactivation of an intercalator other than by direct photoactivation by UV light, although use of a UV light probe or X-rays is suggested for penetrating deeper into tissues. No examples are provided for the use of a UV light probe or for use of X-rays. No example of any stimulation by X-ray radiation is taught.

PUVA

Methoxypsoralen (8MOP) is a linear tricyclic molecule that readily enters cell nuclei where it intercalates DNA at pyrimidine-purine sites [1]. Following photo-activation by UV irradiation, a combination referred to as PUVA, 8MOP interacts with pyrimidines to form stable DNA monoadducts. Upon further UVA treatment, a percentage of monoadducts can then be converted to interstrand DNA crosslinks (ICL), which in turn inhibit transcription and DNA replication [1,2]. Importantly, the anti-proliferative effects of PUVA appear to be related to the formation of ICL, rather than monoadducts. Because of its anti-proliferative effects, PUVA has been used to treat hyperproliferative skin conditions including psoriasis [3]. Furthermore, T lymphocytes-normal and malignant-appear to be particularly sensitive to the anti-proliferative effects of PUVA therapy; hence, the use of PUVA as a treatment for cutaneous T-cell lymphoma and graft-versus-host disease [4-6].

In addition to playing a role in the formation of ICL, there is evidence that psoralen may also target non-nuclear proteins, lipids, and cellular membrane components [7-9]. For example, Laskin et al used psoralen derivatives incapable of forming DNA adducts in response to UV irradiation to show that PUVA treatment blocked the mitogenic effects of soluble Epidermal Growth Factor (EGF) on its cognate cell surface receptor, EGF Receptor (EGFR) [7,9]. Interestingly, inhibition of EGFR phosphorylation in response to PUVA was not mediated through a direct psoralen-EGFR interaction, but rather psoralen interacting with a lower molecular weight binding protein.

ErbB family receptors are Class I receptor tyrosine kinases (Grassot J, Mouchiroud G, Perrière G., RTKdb: database of Receptor Tyrosine Kinase, *Nucleic Acids Res.*, 31(1): 353-8 (2003))). ERBB2 (also known as HER-2 or NEU) appears to act as an essential partner for the other members of the family without itself being activated by a cognate ligand (Graus-Porta D, Beerli. RR, Daly J M, Hynes N E, ErbB-2, the preferred heterodimerization partner of all ErbB receptors, is a mediator of lateral signaling, *EMBO J.*, 16(7):1647-55 (1997)). Ligands of the ErbB family of receptors are peptides, many of which are generated by proteolytic cleavage of cell-surface proteins. HER/ErbB is the viral counterpart to the receptor tyrosine kinase EGFR. All family members heterodimerize with each other to activate downstream signaling pathways and are aberrantly expressed in many cancers, particularly forms of breast cancer.

Similar to EGFR, the ErbB2 oncogene is a member of the type 1 transmembrane family of receptor tyrosine kinases. Gene amplification and overexpression of ErbB2, which occurs in 25% of all breast cancers, predicts for a poor clinical outcome as a consequence of increased tendency to metastasize to visceral organs earlier in the disease course [10,11]. These findings have prompted the development of ErbB2 targeted therapies-biological and small molecule tyrosine kinase inhibitors (TKIs)—for the treatment of early and advanced stage ErbB2+ breast cancers [12]. Although ErbB2 targeted therapies represent a significant advancement in the treatment of aggressive breast cancers, their clinical efficacy has been limited by the inevitable development of therapeutic resistance, particularly in the advanced stage setting [13-15].

Using mass spectroscopy and biochemical approaches, the inventors have now shown for the first time that photoactivated 8MOP can directly interact with regulatory elements within the ErbB2 catalytic kinase domain, providing a likely explanation for the targeted inhibition of ErbB2 signaling in response to PUVA therapy. Furthermore, a modified psoralen derivative that lacks the ability to cross-link DNA maintained its ability to block ErbB2 signaling and induce tumor cell apoptosis. The inventors have also shown that PUVA can trigger significant apoptosis in ErbB2+ breast cancer models of acquired therapeutic resistance to lapatinib and similar ErbB2 targeted therapies. These findings affect the development of new therapeutic strategies for ErbB+ breast cancers, including those that have become resistant to existing ErbB2 targeted therapies.

SUMMARY OF THE INVENTION

Accordingly, one object of the present invention is to provide a method for treatment of a cell proliferation disease or disorder with a psoralen derivative and combination therapy.

A further object of the present invention is to provide a method of treating a cell proliferation disorder or disease with a psoralen derivative lacking a DNA cross-linking motif and radiation energy.

A further object of the present invention is to provide a method of treating a cell proliferation disorder or disease with a psoralen or psoralen derivative, lapatinib and radiation energy.

A further object of the present invention is to provide a method of treating a cell proliferation disorder or disease with a psoralen or psoralen derivative, neratinib and radiation energy.

A still further object of the present invention is to provide a method of inhibition of ErbB2 signaling in cancer cells with a psoralen derivative lacking a DNA cross-linking motif and radiation energy.

These and other objects of the present invention, which will become more apparent in conjunction with the following detailed description of the preferred embodiments, either alone or in combinations thereof, have been satisfied by the discovery of a method of treating a cell proliferation disorder or disease comprising administering a psoralen derivative lacking a DNA cross-linking motif or a combination of a psoralen or its derivative and lapatinib or neratinib to a subject in need thereof and applying initiation radiation energy form an energy source.

BRIEF DESCRIPTION OF THE FIGURES

The patent or application file contains at least one drawing executed in color. Copies of this patent or patent application publication with color drawing(s) will be provided by the office upon request and payment of the necessary fee.

A more complete appreciation of the invention and many of the attendant advantages thereof will be readily obtained as the same becomes better understood by reference to the following detailed description when considered in connection with the accompanying drawings, wherein:

FIG. 3 A-C show inhibition of ErbB2 signaling in response to PUVA is independent of DNA crosslinking. The chemical structures of (A) 8MOP, and (B) 7-methylpyridopsoralen (SMSF032310), which is a derivative of 8MOP that lacks the ability to crosslink DNA, are shown. (C) BT474 and SKBR3 cells were exposed to the indicated treatments. Cell growth and viability assays were performed after 72 hr. P<0.0003 (SKBR3); P<0.0009 (BT474). Cells treated with vehicle alone served as controls. Results represent the mean+/−standard error of triplicate samples, and are representative of three independent experiments. Corresponding Western blot analysis of the indicated protein/phosphoproteins is shown. Steady-state actin protein levels served as controls for equal loading of proteins. Results are representative of three independent experiments.

FIG. 4 A-B show that 8MOP interacts with the catalytic kinase domain of ErbB2. (A) 8MOP interacts with three peptide regions within the ErbB2 catalytic kinase domain. Qualitative peptide identifications within the ErbB2 catalytic kinase domain following LC-MS/MS analysis of a streptavidin pull-down of biotinylated-8MOP bait (see Material and Methods). The transmembrane domain is indicated (red diamond) and the five C-terminus tyrosine autophosphorylation sites are indicated (p). (B) Non-reducing Western blot analysis of the interaction of 8MOP with ErbB2. BT474 cells were treated with 800dye-8MOP (Promega) or with vehicle (0.01% DMSO) alone served as control for 48 hr and then exposed to UV irradiation (2J) prior to Western blot analysis. The image on the left shows the Western blot for ErbB2 (red). The image on the right shows the same membrane directly scanned for the presence of 800dye-8MOP (green), which overlays the ErbB2 signal. The results are representative of three independent experiments.

DETAILED DESCRIPTION OF THE INVENTION

Figure 1:
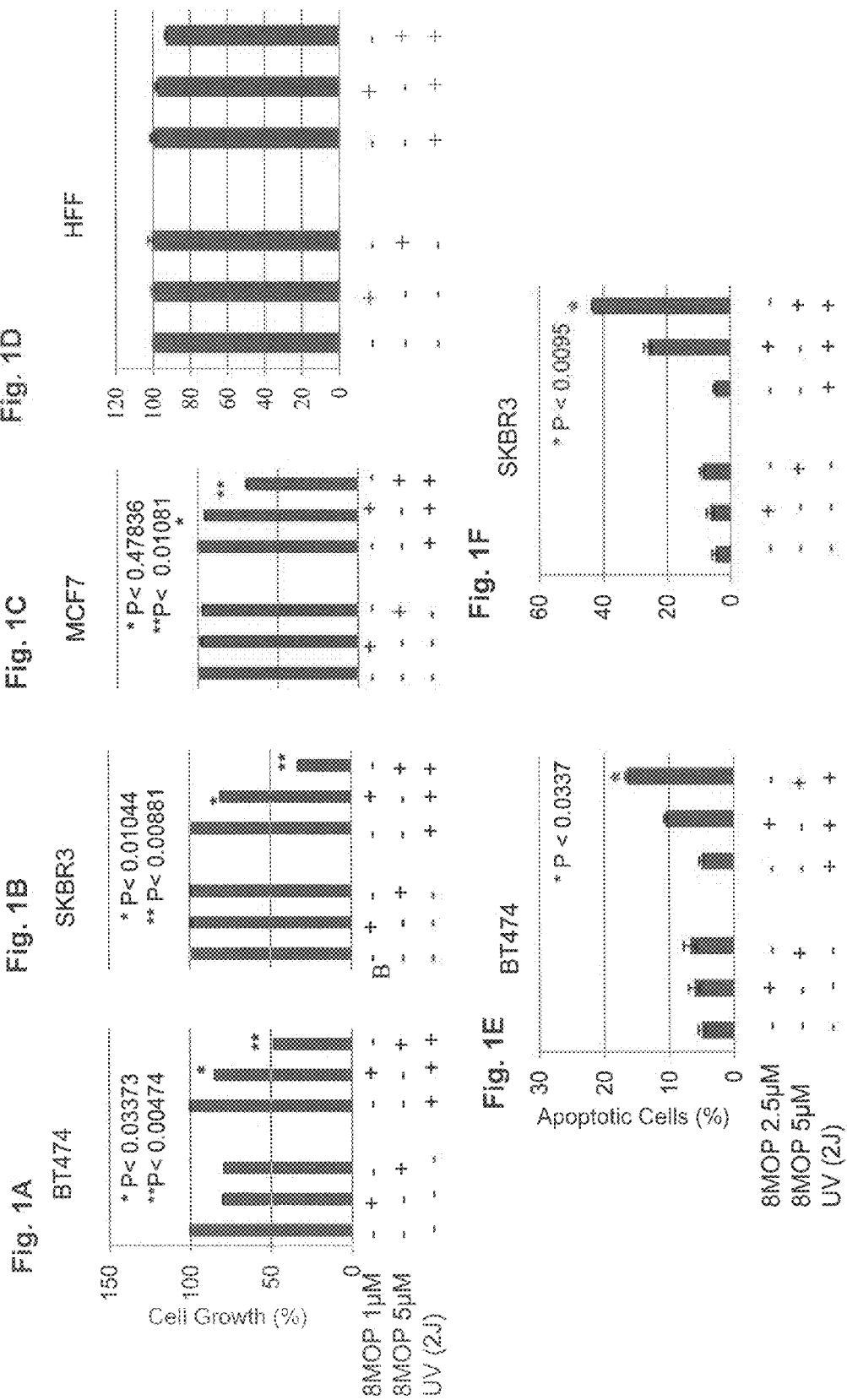
FIG. 1 A-F show PUVA antitumor activity in HER2+ breast cancer cells. Cells were pre-treated with the indicated concentrations of 8MOP for 4 hr before UVA irradiation (2J), and then cultured for an additional 72 hr before being analyzed for cell growth (A) BT474; (B) SKBR3; (C) MCF7, (D) HFF and apoptosis (D) BT474; (E) SKBR3. Cells treated with vehicle (0.01% DMSO) alone served as controls. Results represent the mean+/−standard error of triplicate samples, and are representative of three independent experiments.

All publications, patent applications, patents, and other references mentioned herein are incorporated by reference in their entirety. Further, the materials, methods, and examples are illustrative only and are not intended to be limiting, unless otherwise specified.

The present invention sets forth novel methods of treating cell proliferation disorders that is effective, specific, and has few side-effects. Those cells suffering from a cell proliferation disorder are referred to herein as the target cells. A treatment for cell proliferation disorders, including solid tumors, is capable of chemically binding cellular nucleic acids, including but not limited to, the DNA or mitochondrial DNA or RNA of the target cells. For example, a photoactivatable agent, such as a psoralen or a psoralen derivative, is exposed in situ to an energy source capable of activating the photoactivatable agent or agents selected. In another example, the photoactivatable agent is a photosensitizer. The photoactivatable agent may be a metal nanocluster or a molecule.

As noted above, an object of the present invention is to treat cell proliferation disorders. Exemplary cell proliferation disorders may include, but are not limited to, cancer, as well as bacterial and viral infections where the invading bacteria grows at a much more rapid rate than cells of the infected host. In addition, treatment for certain developmental stage diseases related to cell proliferation, such as syndactyly, are also contemplated.

Accordingly, in one embodiment, the present invention provides methods that are capable of overcoming the shortcomings of the existing methods. In general, a method in accordance with the present invention utilizes the principle of energy transfer to and among molecular agents to control delivery and activation of pharmaceutically active agents such that delivery of the desired pharmacological effect is more focused, precise, and effective than the conventional techniques.

Although not intending to be bound by any particular theory or be otherwise limited in any way, the following theoretical discussion of scientific principles and definitions are provided to help the reader gain an understanding and appreciation of the present invention.

As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

As used herein, an "activatable pharmaceutical agent" is an agent that normally exists in an inactive state in the absence of an activation signal. When the agent is activated by a matching activation signal under activating conditions, it is capable of effecting the desired pharmacological effect on a target cell (i.e. preferably a predetermined cellular change).

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof.

Activation of the agent may be as simple as delivering the signal to the agent or may further premise on a set of activation conditions. For example, in the former case, an activatable pharmaceutical agent, such as a photosensitizer, may be activated by UV-A radiation. Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

In one preferred embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, or a combination thereof.

As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In preferred embodiments, the energy modulation agent receives higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as a lipid, chitin or chitin-derivative, a chelate or other functionalized carrier that is capable of concentrating the UV-A emitting source in a specific target tumor.

Additionally, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

The energy emitting source can be any energy source capable of providing energy at a level sufficient to activate the activatable agent directly, or to provide the energy modulation agent with the input needed to emit the activation energy for the activatable agent (indirect activation). Preferable initiation energy sources include, but are not limited to, UV-A lamps or fiber optic lines, a light needle, an endoscope, and a linear accelerator that generates x-ray, gamma-ray, or electron beams. In a preferred embodiment the initiation energy source is a source of energy capable of penetrating completely through the subject. Within the context of the present invention, the phrase "capable of penetrating completely through the subject" is used to refer to sources of energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, x-rays, gamma rays, electron beams, microwaves and radio waves.

Alternatively, the energy emitting source may be another energy modulation agent that emits energy in a form suitable for absorption by the transfer agent. For example, the initiation energy source may be acoustic energy and one energy modulation agent may be capable of receiving acoustic energy and emitting photonic energy (e.g. sonoluminescent molecules) to be received by another energy modulation agent that is capable of receiving photonic energy. Other examples include transfer agents that receive energy at x-ray wavelength and emit energy at UV wavelength, preferably at UV-A wavelength. As noted above, a plurality of such energy modulation agents may be used to form a cascade to transfer energy from initiation energy source via a series of energy modulation agents to activate the activatable agent.

Signal transduction schemes as a drug delivery vehicle may be advantageously developed by careful modeling of the cascade events coupled with metabolic pathway knowledge to sequentially or simultaneously activate multiple activatable pharmaceutical agents to achieve multiple-point alterations in cellular function.

Photoactivatable agents may be stimulated by an energy source, such as irradiation, resonance energy transfer, exciton migration, electron injection, or chemical reaction, to an activated energy state that is capable of effecting the predetermined cellular change desired. In a preferred embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

Ultraviolet A activation of psoralen, a therapy referred to as PUVA, is an effective treatment for non-malignant and malignant proliferative skin disorders. The mechanism of action has been attributed to psoralen intercalation of DNA, which upon UV treatment, leads to formation of interstrand DNA crosslinks (ICL), and induction of cell apoptosis. Here, the inventors have discovered a new mechanism of action of PUVA in models of breast cancer that overexpress the ErbB2 receptor tyrosine kinase oncogene. PUVA blocked tyrosine autophosphorylation/activation of ErbB2 with concomitant inhibition of downstream PI3K and MAPK signaling pathways, triggering tumor cell apoptosis. Importantly, photoactivation of a modified psoralen derivative, 7-methylpyridopsoralen (SMSF032310)

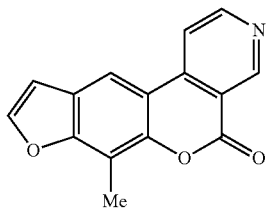

(SMSF032310)

that lacks the DNA cross-linking motif retained the ability to block ErbB2 signaling and induce tumor cell death. Using a mass spectroscopy-based platform, the inventors have shown that 8-MOP (8-methoxypsoralen) can interact with the catalytic kinase domain of ErbB2. Importantly, the antitumor effects of PUVA do not appear to be cross resistant with other ErbB2 targeted therapies, as PUVA can induce apoptosis in established ErbB2+ cancer models of acquired lapatinib resistance. Thus, PUVA represents a novel ErbB2 targeted therapy for the treatment of ErbB2+ breast cancers, including those that have developed resistance to other ErbB2 targeted therapies.

A preferred method of inhibition of ErbB2 signaling in cancer cells comprises applying a psoralen derivative lacking a DNA cross-linking motif to cancer cells and applying initiation radiation energy form an energy source, thereby blocking the ErbB2 signaling. In one embodiment the cancer cells may be ErbB2+ breast cancer cells.

The psoralen derivative lacking a DNA cross-linking motif is preferably a psoralen derivative of Formula (I):

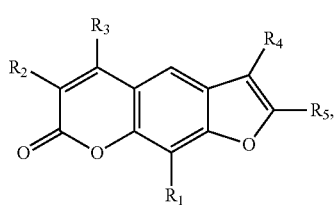

(I)

wherein $R_1$ is hydrogen, lower alkyl, or lower alkoxy;

$R_2$ and $R_3$ are each, independently, hydrogen, $C_1$-$C_6$ alkyl, or $C_1$-$C_6$ alkoxy, or $R_2$ and $R_3$ may join to form a substituted or unsubstituted, condensed 5 to 7 membered aliphatic or aromatic ring, optionally containing a heteroatom selected from N, S, or O;

$R_4$ and $R_5$ are each, independently, hydrogen, $C_1$-$C_6$ alkyl, or $C_1$-$C_6$ alkoxy, or $R_4$ and $R_5$ may join to form a substituted or unsubstituted, condensed 5 to 7 membered aliphatic or aromatic ring, optionally containing a heteroatom selected from N, S, or O;

With the proviso that at least one of $R_2$ and $R_3$ or $R_4$ and $R_5$ must be substituents sufficient to prevent the formation of DNA cross-links, preferably at least one of $R_2$ and $R_3$ or $R_4$ and $R_5$ join to form a substituted or unsubstituted, condensed 5 to 7 membered aliphatic or aromatic ring, optionally containing a heteroatom selected from N, S, or O.

In a preferred embodiment, $R_2$ and $R_3$ or $R_4$ and $R_5$ join to form a condensed aromatic heterocycle, most preferably a pyridyl ring. A most preferred embodiment of compound in which DNA crosslinking is blocked is 7-methylpyridopsoralen having the following structure:

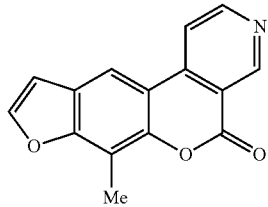 [SMILES: Cc1c2occc2cc2c1oc(=O)c1cnccc12]

In another embodiment, prior to applying the initiation energy, at least one energy modulation agent that converts the initiation energy to an energy that activates the psoralen derivative, is administered to the subject.

In yet another embodiment, the energy modulation agent may be one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

A preferred method of treating a cell proliferation disorder or disease comprises administering a psoralen derivative lacking a DNA cross-linking motif to a subject in need thereof and applying radiation energy form an energy source, wherein the treatment is caused by inducing apoptosis in diseased cells, thereby blocking ErbB2 signaling in cancer cells. The cell proliferation disorder or disease may be cancer and preferably, breast cancer. In one embodiment, the diseased cells may be ErbB2+ breast cancer cells.

In another embodiment, the radiation energy is UVA or visible energy which may be applied directly or indirectly. The initiation energy may be applied via a thin fiber optic.

In another embodiment, prior to said applying the initiation energy, at least one energy modulation agent that converts the initiation energy to an energy that activates the psoralen derivative may be administered. The energy modulation agent may be one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

Another preferred method of treating a cell proliferation disorder or disease comprises administering a psoralen or psoralen derivative and lapatinib to a subject in need thereof and applying radiation energy form an energy source, wherein the treatment reduces diseased cell growth and/or viability compared to that of diseased cells treated with lapatinib alone, or a combination of lapatinib and the psoralen or psoralen derivative, or a combination of lapatinib and the radiation energy. In one embodiment, the treatment reduces tumor cell growth and/or viability in lapatinib resistant tumor cells.

The cell proliferation disorder or disease may be breast cancer. In another embodiment, the lapatinib resistant tumor cells may be HER2+ breast cancer cells.

In yet another embodiment, the radiation energy is UVA or visible energy which may be applied directly or indirectly.

In another embodiment, a psoralen or psoralen derivative is 8-Methoxypsoralen (8-MOP).

In a different embodiment, prior to said applying the initiation energy, at least one energy modulation agent that converts the initiation energy to an energy that activates the psoralen derivative may be administered to a subject. The energy modulation agent may be one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

Yet, another preferred method of treating a cell proliferation disorder or disease comprises administering a psoralen or psoralen derivative and neratinib to a subject in need thereof and applying radiation energy form an energy source, wherein the treatment reduces diseased cell growth and/or viability compared to that of diseased cells treated with neratinib alone, or a combination of neratinib and the psoralen or psoralen derivative, or a combination of neratinib and the radiation energy.

In one embodiment, the diseased cells may be tumor cells. The cell proliferation disorder or disease may be breast cancer. In one embodiment, the tumor cells may be ErbB2+ breast cancer cells.

In another embodiment, the radiation energy is UVA or visible energy which may be applied directly or indirectly.

In a different embodiment, a psoralen or psoralen derivative is 8-Methoxypsoralen (8-MOP).

In yet another embodiment, prior to said applying the initiation energy, at least one energy modulation agent that converts the initiation energy to an energy that activates the psoralen derivative is administered to the subject. The energy modulation agent is one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

DISCUSSION

The molecular basis for the anti-proliferative effects of photo-activated psoralen in the treatment of benign and neoplastic skin diseases has historically been attributed to the formation of interstrand DNA crosslinks that lead to inhibition of transcription and DNA replication. T cells, which mediate many of the dermatological indications for PUVA e.g. graft-versus-host disease; cutaneous T cell lymphoma seem to be particularly sensitive to the anti-proliferative effects of PUVA and have therefore served as a frequently used model to study the biological effects of PUVA therapy [4-6]. In contrast, there has been relatively little scientific evidence to support the use of PUVA therapy in the treatment of solid tumors. Here, the inventors have shown for the first time that PUVA therapy can directly target the catalytic kinase domain of the ErbB2 receptor tyrosine kinase oncogene. The interaction of photo-activated 8MOP with regulatory elements within the ErbB2 catalytic kinase domain may explain the marked inhibition of ErbB2 signaling in PUVA-treated ErbB2+ breast cancer cells, including those that have developed resistant to current FDA-approved ErbB2 targeted therapies.

The interaction between 8MOP and ErbB2 was demonstrated using two independent strategies: (i) LC/MS/MS; and (ii) Western blot analysis. These findings were further supported by the observation that a DNA non-crosslinking psoralen derivative maintained its ability to block ErbB2 signaling and induce tumor cell apoptosis. The ErbB2+ breast cancer cell lines used in these studies express EGFR, which has also been shown to be a target of PUVA therapy [9]. However, survival of parental BT474 and SKBR3 cells is not dependent upon EGFR, but instead, dependent upon signaling via ErbB2-ErbB3 heterodimers [16]. The inventors' data suggest that the antitumor effects of PUVA therapy in parental ErbB2+ breast cancer cells were mediated through direct effects on ErbB2. Moreover, non-malignant HFF cells that express wild-type EGFR were less sensitive to the apoptotic effects of PUVA, consistent with the notion that EGFR is not responsible for induction of apoptosis in PUVA-treated ErbB2+ breast cancer cells (FIG. 1D).

Of particular interest is the antitumor activity of PUVA therapy in ErbB2+ breast cancer models of acquired therapeutic resistance to lapatinib and other ErbB2 targeted therapies. It is worth noting that acquired therapeutic resistance to lapatinib does not appear to be mediated by reactivation of ErbB2 signaling. In fact, ErbB2 phosphorylation remains inhibited in resistant cells [16,18]. Importantly, targeted molecular knockdown of ErbB2 does not reverse lapatinib resistance [18], indicating that survival of resistant cells is no longer dependent upon ErbB2 alone, at least not the 185 kDa full-length form of ErbB2 ($p185^{ErbB2}$) expressed at the cell surface. Instead, the viability of lapatinib resistant ErbB2+ breast cancer cells is dependent upon other factors. For example, we have shown that resistant cells express a truncated form of ErbB2, referred to as $p85^{ErbB2}$, which can be generated by alternate initiation of translation [20] and/or proteolytic processing of $p185^{ErbB2}$ [17]. Moreover, $p85^{ErbB2}$ is preferentially expressed in tumor cell nuclei. This nuclear, truncated form of ErbB2 lacks the extracellular (ECD) and transmembrane domains, while retaining the full cytoplasmic domain, including the catalytic kinase domain and tyrosine autophosphorylation sites. Expression of $p85^{ErbB2}$ driven by a heterologous promoter renders ErbB2+ breast cancer cells that are normally sensitive to the antitumor effects of lapatinib, resistant to lapatinib and other ErbB2 targeted therapies. Although the exact mechanism of $p85^{ErbB2}$ action is unknown, it, in contrast to $p185^{ErbB2}$ and $p110^{ErbB2}$—a membrane-bound form of ErbB2 that lacks the ECD-does not appear to activate cytoplasmic protein kinase signaling cascades [17]. The inventors have shown that tyrosine phosphorylation of $p85^{ErbB2}$ is not inhibited by lapatinib or similar TKIs in class. The inventors have now shown that PUVA therapy blocks $p85^{ErbB2}$ phosphorylation, triggering apoptosis. One potential explanation is that lapatinib cannot access the ATP binding groove of $p85^{ErbB2}$. In contrast, the ability of 8MOP to access nuclear targets e.g. DNA, is well-established. It is therefore possible that 8MOP more readily accesses, and blocks the catalytic kinase domain of $p85^{ErbB2}$.

The inventors recently showed that development of lapatinib resistance can be mediated through a switch in the regulation of cell survival from ErbB2-ErbB3-PI3K signaling in treatment naïve ErbB2+ breast cancer cells to ErbB3-EGFR-PI3K-PDK1-Akt (T308) signaling axis in the resistant setting, the latter driven in part through autocrine production of the ErbB3 ligand heregulin β1 [16]. Although the exact mechanism(s) underlying the antitumor effects of PUVA is unknown, persistent phosphorylation of Akt T308, which was seen in models of lapatinib resistance [16], was inhibited by PUVA. In addition, total EGFR and ErbB3 were reduced in PUVA-treated resistant cells. These findings are interesting in light of a recent study showing that several ErbB TKIs can induce proteolysis of targeted receptor(s) in a manner similar to hsp90 antagonists [21]. Induction of receptor proteolysis by TKIs, including lapatinib, was shown to be mediated through ATP competitive binding with cdc37, the latter stimulating binding between the client protein e.g. ErbB2 and hsp90. It is therefore possible that PUVA therapy may also trigger degradation of EGFR, ErbB2, and ErbB3 by blocking access of the cdc37/hsp90 complex to client proteins ErbB receptors.

The inventors propose that 8-MOP interacts with the ErbB2 catalytic kinase domain at amino acid residues distinct from lapatinib. Although structural analysis of a lapatinib-EGFR complex has been reported, there has been no structural analysis of a lapatinib-ErbB2 complex. Most of the amino acid residues associated with the regulation of the ErbB2 catalytic kinase activity are located in the vicinity of the ATP binding groove within the deep cleft located between the N- and C-terminal lobes of the ErbB2 receptor [22]. The inventors have found that 8MOP interacts with peptides located within the DFG motif and activation loop of the C-lobe, both of which are involved in regulating ErbB2 autokinase activity [22]. The structural analysis of lapatinib-EGFR crystals suggests that lapatinib likely interacts with amino acid residues within the ATP binding groove distinct from those of photo-activated 8MOP [22]. It is possible therefore that photo-activated 8-MOP binds to the catalytic kinase domain, blocking its activity and triggering proteolysis of the receptor in a manner similar to irreversible ErbB TKIs e.g. neratinib.

Targeted therapies are increasingly being used in combination with other targeted and cytotoxic drugs [23]. The inventors were interested in finding out whether other targeted therapies might enhance the antitumor activity of PUVA therapy. In this regard, a recent study found that the combination of a histone deacetylase (HDAC) inhibitor and PUVA led to enhanced antitumor activity compared with either treatment alone [24]. When the inventors examined the effects of adding targeted therapies, including HDAC and PI3K inhibitors, to PUVA therapy, wthey found that neratinib, at sub-lethal doses alone, significantly increased apoptosis in ErbB2+ breast cancer cells when combined with PUVA. It is known that neratinib has promiscuous inhibitory activity against non-ErbB kinases, including MAP kinase family members. It is possible that the enhanced antitumor effect observed with the addition of neratinib to PUVA might be directly or indirectly related to inhibition of a kinase(s) involved in DNA repair of ICL, thereby sensitizing tumor cells to the DNA damaging effects of PUVA.

The data presented here suggests that the antitumor effects of PUVA can be mediated through DNA-independent mechanisms. It is possible that inhibition of the ErbB2 signaling axis may sensitize tumor cells to the DNA damaging effects of PUVA therapy by inhibiting P3K-Akt regulated DNA damage repair enzymes. In this context, ErbB2 targeted therapies have previously been shown to sensitize tumor cells to radiation therapy [25]. Therefore, therapeutic interventions, including PUVA alone or in combination with ErbB targeted therapies such as neratinib that can simultaneously damage DNA and also block ErbB-regulated survival pathways including those that repair damaged DNA, represent an attractive therapeutic strategy in treatment naïve ErbB2+ tumors and those that have developed resistance to ErbB2 targeted therapies through activation of alternate pathways e.g. ErbB3-EGFR-PDK1-Akt (T308) signaling axis, and express nuclear truncated ErbB2 receptors that elude the inhibition by existing ErbB2 targeted therapies.

Having generally described this invention, a further understanding can be obtained by reference to certain specific examples which are provided herein for purposes of illustration only and are not intended to be limiting unless otherwise specified.

EXAMPLES

Cell Culture and Reagents

ErbB2+(BT474; SKBR3) and ErbB2 negative (MCF-7; T47D) human breast cancer cell lines, and the human foreskin fibroblast (HFF) cell line were obtained from the American Type Culture Collection (Manassas, Va.). Lapatinib resistant breast cancer cells (rBT474; rSKBR3) were generated and maintained in culture as previously described [16-18]. Cells were maintained in RPMI-1640 supplemented with 10% fetal bovine serum and L-glutamine from GIBCO (Grand Island, N.Y.) growing in a humidified atmosphere of 5% $CO_2$ at 37° C. IRDye 800 conjugated affinity purified anti-rabbit IgG and anti-mouse IgG were from Rockland (Gilbertsville, Pa.). Alexa Fluor 680 goat anti-rabbit IgG were purchased from Molecular Probes (Eugene, Oreg.). Anti-PARP (Poly (ADP-ribose) Polymerase) monoclonal antibody was from BD PharMingen (San Jose, Calif.). 8-Methoxypsoralen (8MOP) and the 4G10 anti-phosphotyrosine (p-tyr) antibody were purchased from Sigma-Aldrich (St. Louis, Mo.). Monoclonal antibodies to c-ErbB2 and EGFR were purchased from Neo Markers (Union City, Calif.). PARP cleavage product was obtained from Cell Signaling (Beverly, Mass.). Antibodies to Akt1/2, phospho-Akt1/2 (S473), phospho-Akt1/2 (T308), phospho-Erk1/2 and Erk1/2 were purchased from Santa Cruz (Santa Cruz, Calif.). Lapatinib (GW572016) and neratinib (HKI-272) [19] were purchased from LC Laboratories (Woburn, Calif.).

UV Irradiation, Growth/Viability and Apoptosis Assays

UV irradiation was carried out in 6 or 96 well plate format in a UV Stratalinker 1800 (Statagene, LA Jolla, Calif.) at the UV doses indicated in the figures. Cell growth and viability assays were performed in a 96-well plate format in a final volume of 100 µl/well using the cell proliferation reagent WST-1 from Roche Diagnostics (Mannheim, Germany), as previously described [16-18]. Details of the apoptosis assay have been previously described [16-18]. Briefly, cells were treated in 12-well plates with 8MOP, UV irradiation, or lapatinib at the treatment conditions indicated in the Figure legends. Cells were harvested with trypsin-EDTA, and 5000 cells in final volume of 50 µl were sampled in 96-well microplates. Cells were directly stained with annexin V-PE and nexin 7-AAD in 1× Nexin Buffer in a 200 µl final reaction volume. After incubating at room temperature for 20 min, the reaction samples were analyzed in the Guava PCA-96-system (Guava Technology Inc. Hayward, Calif.).

SDS-PAGE and Western Blot Analysis

Whole cell extracts were prepared by scraping cells off petri dishes, washing cell pellets 2× in phosphate buffered saline (PBS), and then re-suspending pellets in two-packed-cell volumes of RIPA buffer (150 mM NaCl, 50 mM Tris-HCl, pH 7.5, 0.25% (w/v) deoxycholate, 1% NP-40, 5 mM sodium orthovanadate, 2 mM sodium fluoride, and a protease inhibitor cocktail). Protein concentrations were determined using a modification of the Bradford method (Bio-Rad Labs, Hercules, Calif.). For Western blot analysis, equal amounts of proteins (25 to 50 µg) were resolved by either 7.5% or 4-15% gradient SDS polyacrylamide gel electrophoresis under reducing conditions as previously described [16-18]. Proteins were transferred to nitrocellulose membranes and probed with primary antibodies specific for proteins of interest. After extensive washing, membranes were incubated with a secondary IRDye 800 conjugated anti-rabbit or mouse IgG, or Alexa Fluor 680 anti-rabbit IgG and proteins were visualized using the LI-COR Odyssey Infrared Imaging System (LI-COR, Inc., Lincoln, Nebr.).

Protein Pull-Down and Nano-Flow Liquid Chromatography Electrospray Ionization Tandem Mass Spectrometry (LC-MS/NIS) Analysis BT474 cells were pre-treated with 5 µM biotin-linked 8-MOP for 24 hr before being irradiated with 1 J UVA. After UVA irradiation, cells were harvested and whole cell lysates were prepared in RIPA buffer. After centrifugation, a 30 µl suspension of M-280 Streptavidin Dynabeads® (Invitrogen, Carlsbad, Calif.) was added to each 130 µl crude lysate sample. The resulting mixtures were placed on an orbital vortex mixer for 20-30 min. The samples were then magnetized and the supernatants removed and discarded. A solution of 0.01% (v/v) Tween 20 in PBS (150 µl) was added to each sample and the resulting mixtures were placed on orbital vortex mixer for 20-30 min. The samples were then magnetized and the supernatants were removed and discarded. Next a solution of 0.1% (v/v) SDS in PBS (150 µl) was added to each sample and the resulting mixtures were heated to 50° C. for 15 min. The samples were magnetized and supernatants removed and discarded, after which 150 µl of 50 mM ammonium bicarbonate was added to each sample, and the mixtures placed on orbital vortex mixer for 20-30 min. The samples were again magnetized and the supernatants removed and discarded. The samples were suspended in 130 µl ammonium bicarbonate (50 mM) prior to mass spectroscopy analysis. Following a pull-down of biotinylated-drug on immobilized streptavidin magnetic beads, samples were washed three times with 200 µl 50 mM ammonium bicarbonate, pH 8. Sample volume was brought to 100 µl 50 mM ammonium bicarbonate (pH 8), and supplemented with Rapigest surfactant (Waters Corporation, Milford, Mass.) to a final concentration of 0.1%. Following disulfide reduction with 5 mM dithiolthreitol at 40° C. for 20 min, free sulfhydryls were alkylated with 10 mM iodoacetamide at room temperature for 45 min. Approximately, 500 ng of sequencing grade modified trypsin (Promega Corporation, Madison, Wis.) was added to each sample and on-resin digestion was allowed to occur for 18 hr at 37° C. with orbital shaking. Supernatants were then collected from each sample after centrifugation at 1000 g for 2 min and Rapigest surfactant was hydrolyzed by acidification to 0.5% trifluoracetic acid (final pH 2.5) for 2 hr at 60° C. Following desalted by C18 Zip-Tip (Millipore) SPE, samples were brought to dryness by vacuum centrifugation and finally resuspended in 10 µl 2% acetonitrile, 0.1% formic acid. Peptide mixtures were subjected to chromatographic separation on a Waters NanoAcquity UPLC (New Objective, Cambridge, Mass.) equipped with a 1.7 µm BEH130 $C_{18}$ 75 µm I.D.×250 mm reversed-phase column. The mobile phase consisted of (A) 0.1% formic acid in water and (B) 0.1% formic acid in acetonitrile. Following a 5 µl injection, peptides were trapped for 5 min on a 5 µm Symmetry $C_{18}$ 180 µm I.D.×20 mm column at 20 µl/min in 99.9% (A). The analytical column was then switched in-line and a linear elution gradient of 5% B to 40% B was performed over 90 min at 300 nL/min. The analytical column was connected to a fused silica PicoTip emitter (New Objective, Cambridge, Mass.) with a 10 µl tip orifice and coupled to a Waters QToF Premier mass spectrometer through an electrospray interface. The instrument was operated in a data-dependent mode of acquisition with the top three most abundant ions selected for MS/MS using a charge state dependent CID energy setting with a 60 s dynamic exclusion list employed. Mass spectra were processed with Mascot Distiller (Matrix Science) and were then submitted to Mascot searches (Matrix Science) against a SwissProt_human database appended with reverse entries at 20 ppm precursor and 0.04 Da product ion mass tolerances with trypsin protease rules selected. Dynamic mass modifications corresponding to oxidation on Met residues were allowed. Searched spectra were imported into Scaffold v2.5 (Proteome Software) and scoring thresholds were set to yield a protein false discovery rate of 0.2% (implemented by the PeptideProphet algorithm) based on decoy database searches.

Gene Transfection of $p85^{ErbB2}$ in Human Breast Cancer Cells

The c-terminal fragment ($p85^{ErbB2}$) was generated based on ErbB2 open reading frames and sub-cloned into the pcDNA3.1 (+) as previously described [17]. HER2 negative T47D breast cancer cells were transfected with the p85 expressing vector using the Lipofectamine™ 2000 Reagent from Invitrogen (Carlsbad, Calif.) as previously described [17]. Stably transfected cells were selected using G418 (400 µg/ml) and the expression level of $p85^{ErbB2}$ was confirmed by western blot analysis as previously described [17].

Statistical Analysis

Data were expressed as means with standard error bars included. Student's t-test was used to determine statistical significance between 2 groups. A value of $p<0.05$ was considered a statistically significant difference.

Example 1

Figure 2:
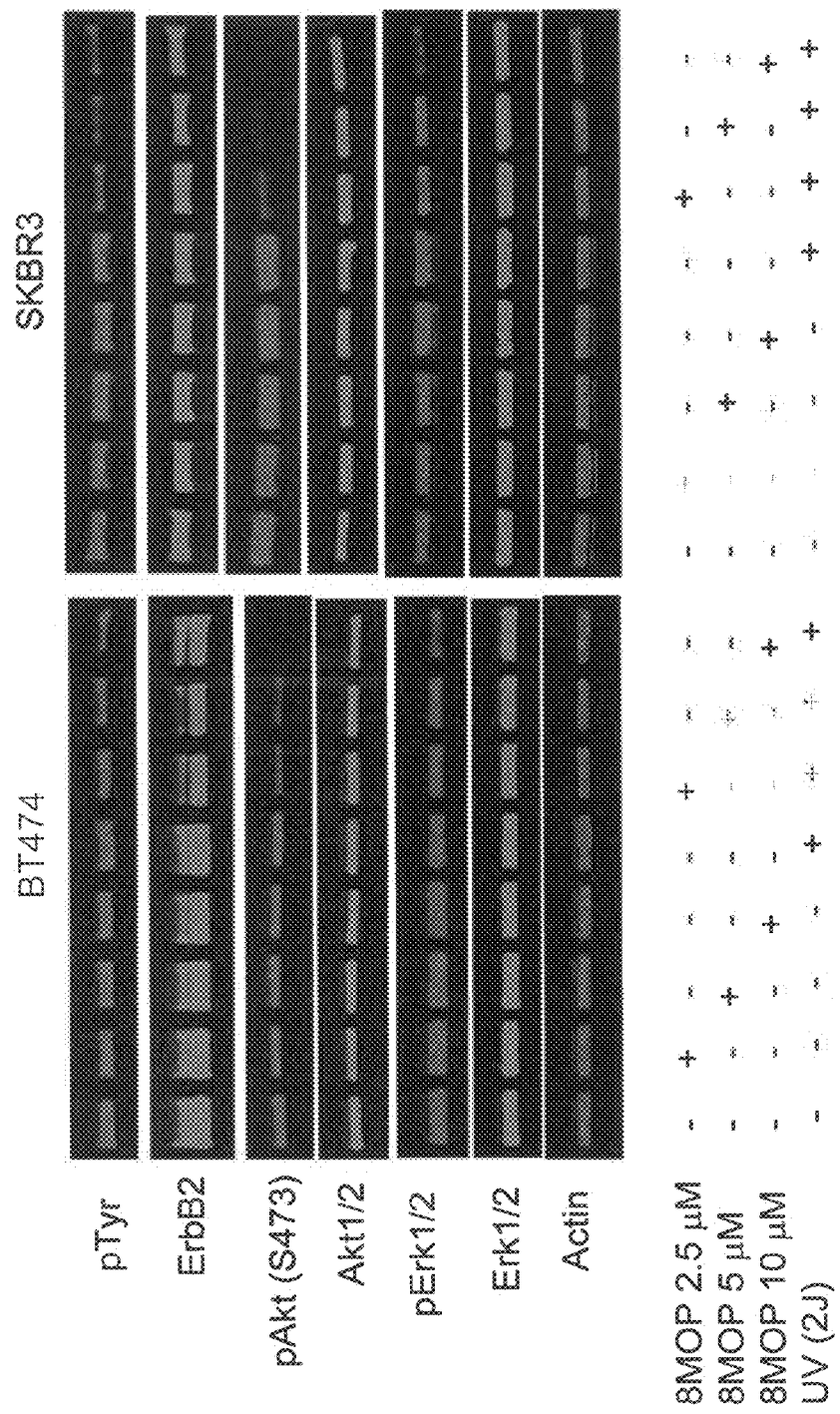
FIG. 2 shows that PUVA therapy inhibits ErbB2 signaling. BT474, SKBR3 and MCF7 cells were subjected to the indicated treatment conditions as described in FIG. 1. Western blot analysis was performed on whole cell lysates. Actin steady-state protein levels served as a control to ensure for equal loading of protein. Results are representative of three independent experiments.

Inhibition of ErbB2 Signaling Triggers Apoptosis in PUVA-Treated ErbB2+ Breast Cancer Cells The growth and viability of ErbB2+ breast cancer cell lines was significantly inhibited by PUVA therapy in a dose-dependent manner (FIGS. 1A and B). The loss of tumor cell viability appeared to be related to induction of apoptosis (FIGS. 1E and F). In contrast, PUVA therapy using identical treatment conditions (2.5 and 5 µM 8MOP) had relatively less effect on the growth and viability of MCF7 cells, a ErbB2 non-overexpressing human breast cancer cell line and a non-malignant human foreskin fibroblast cell line (HFF) (FIGS. 1C and D). It was therefore possible that photo-activated 8MOP might directly modulate ErbB2 activation and signaling. Seeking to demonstrate the effects of PUVA on ErbB2 signaling, the inventors showed that steady-state protein levels of the activated, phosphorylated form of ErbB2 were reduced in PUVA-treated ErbB2+ breast cancer cell lines in a dose-dependent manner (FIG. 2). In addition, total ErbB2 protein levels were reduced in response to higher doses of PUVA therapy. In addition, the activated, phosphorylated forms of Akt and Erk1/2, which are key downstream mediators of the PI3K and MAPK signaling pathways, respectively were also inhibited by PUVA (FIG. 2). In contrast, treatment with the same dose of UV irradiation or 8MOP alone had relatively little effect on cell viability or ErbB2 signaling (FIGS. 1 and 2).

Example 2

Psoralen can Directly Interact with the ErbB2 Catalytic Kinase Domain

A derivative of psoralen, 7-methylpyridopsoralen (FIG. 3A) which lacks the DNA binding motif was synthesized, making it unable to generate ICLs. Next the effects of this compound on ErbB2 signaling and tumor cell viability following UVA irradiation were determined. Upon photo-activation, 7-methylpyridopsoralen significantly inhibited the growth and viability of ErbB2+ breast cancer cells, which correlated with inhibition of phosphorylated and total ErbB2 protein expression (FIG. 3). These findings suggested that interruption of ErbB2 signaling in PUVA-treated tumor cells can be mediated by a mechanism(s) independent of ICL formation. Next is was sought to determine whether 8MOP can directly interact with the catalytic kinase domain of ErbB2. In this regard, BT474 cells were treated with biotinylated-8MOP and a pull-down experiment was performed (see Materials and Methods). Biotinylated-8MOP-protein complexes were isolated from BT474 cell lysate on immobilized streptavidin magnetic beads and subjected to protein digestion using sequencing grade modified trypsin. Peptides were then isolated by LC-MS/MS (see Materials and Methods). We identified three 8MOP bound peptides that corresponded to two sites located within the catalytic kinase domain (aa 861-868; aa 869-883), and one site in the peptide crossover kinase domain (aa 986-1006) (FIG. 4A). As a second independent approach to demonstrate the interaction between 8MOP and ErbB2, BT474 cells were treated with fluorophore-labeled 8MOP (see Materials and Methods) and UVA irradiation. Cell lysates were separated under non-denaturing conditions using native gel electrophoresis. Proteins were transferred to a PVDF membrane, and the fluorophore-labeled 8MOP detected by an Odyssey scanner (FIG. 4B, green). The membrane was then blotted with a primary fluoro-labeled ErbB2 antibody (FIG. 4B, red). The fluoro-conjugated 8MOP was detected at the same molecular weight as large ErbB2 complexes, findings that were consistent with the LC-MS/MS data indicating that 8MOP can directly interact with the ErbB2 receptor.

Example 3

Combination PUVA and Neratinib Treatment Leads to Enhanced Tumor Cell Killing

Figure 5:
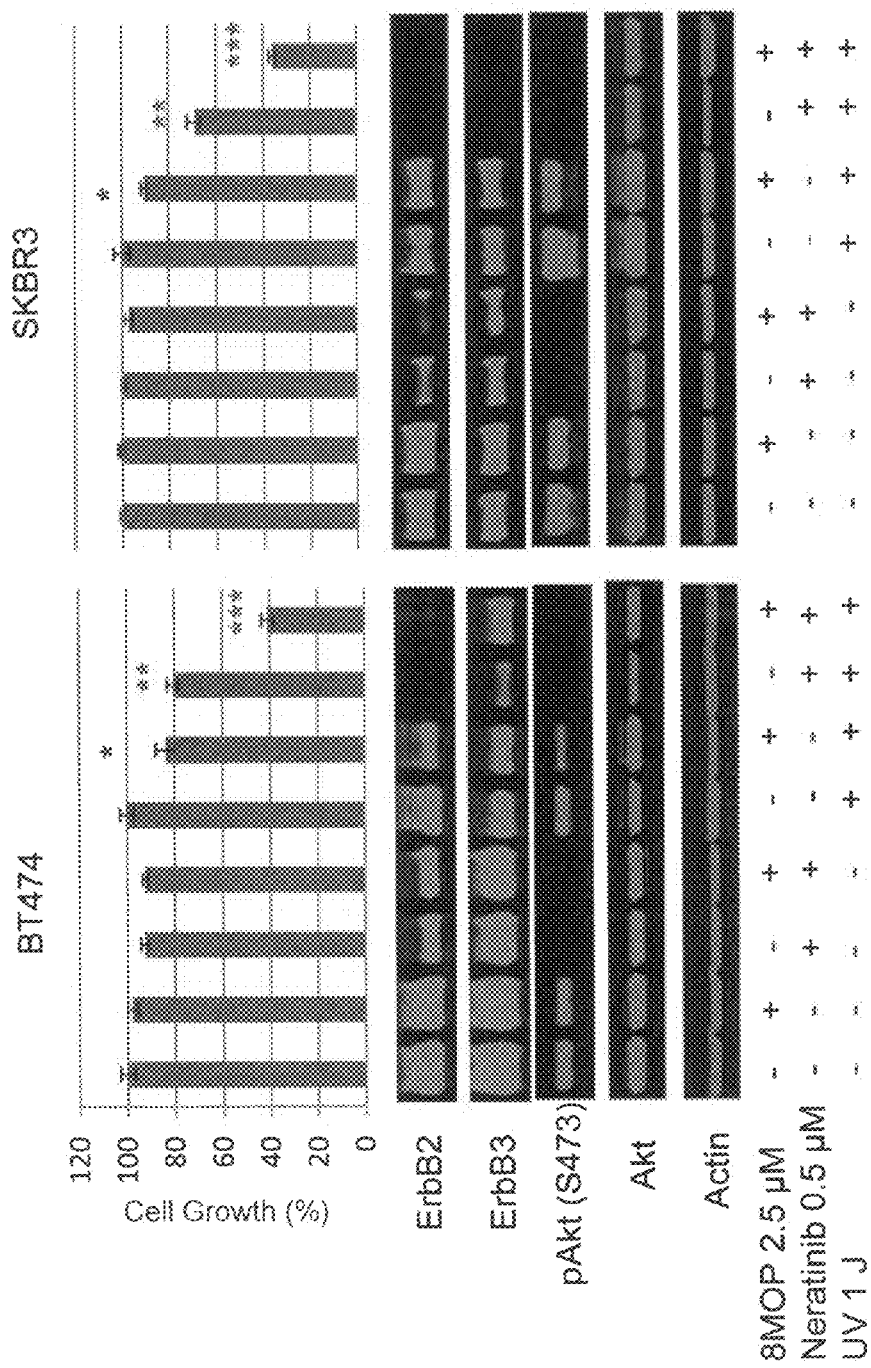
FIG. 5 The combination of PUVA with the irreversible pan-ErbB TKI neratinib results in enhanced antitumor activity. The growth and viability of BT474 and SKBR3 cells (top bar graphs) after being subjected to the indicated treatment conditions. The combination of PUVA plus neratinib: $P<0.0005$ (BT474 and SKBR3 cells). Results represent the mean+/−standard error of triplicate samples, and are representative of three independent experiments. (B) Western blot analysis showing steady-state ErbB2, ErbB3, and phospho-Akt (S473) protein levels in BT474 and SKBR3 cells treated according to the indicated treatment conditions. Vehicle alone (0.01% DMSO) served as a control. Steady-state actin protein levels served as a control for equal loading of protein. The results are representative of three independent experiments.

Targeted therapies tend to be more clinically efficacious in combination with other targeted or cytotoxic drugs. It was therefore evaluated a variety of targeted agents in combination with PUVA including PI3K inhibitors, HDAC inhibitors, PARP inhibitors, and other ErbB TKIs. The most promising combination was with neratinib (HKI-272), a small molecule, irreversible pan-ErbB (ErbB1/EGFR; ErbB2; ErbB3; ErbB4) tyrosine kinase inhibitor that is currently in late phase clinical trials [19]. Treatment of ErbB2+ breast cancer cells with the combination of 8-MOP, UVA irradiation, and neratinib, each at sub-lethal doses when used alone, resulted in significantly enhanced inhibition of cell viability (FIG. 5). The effects of this combination on ErbB2, ErbB3 and downstream signaling pathways were further analyzed. Consistent with the inventors' recent findings [16], it was found that neratinib treatment alone resulted in a marked reduction in total ErbB2 and ErbB3 protein levels, with consequential loss of p-Akt (S473) expression. Interestingly, neratinib in combination with UVA irradiation alone led to further loss of total ErbB2 and ErbB3 protein expression, which was more pronounced in SKBR3 cells (FIG. 5).

Example 4

PUVA Treatment Reverses Lapatinib Resistance in HER2+ Breast Cancer Cells

Figure 6A:
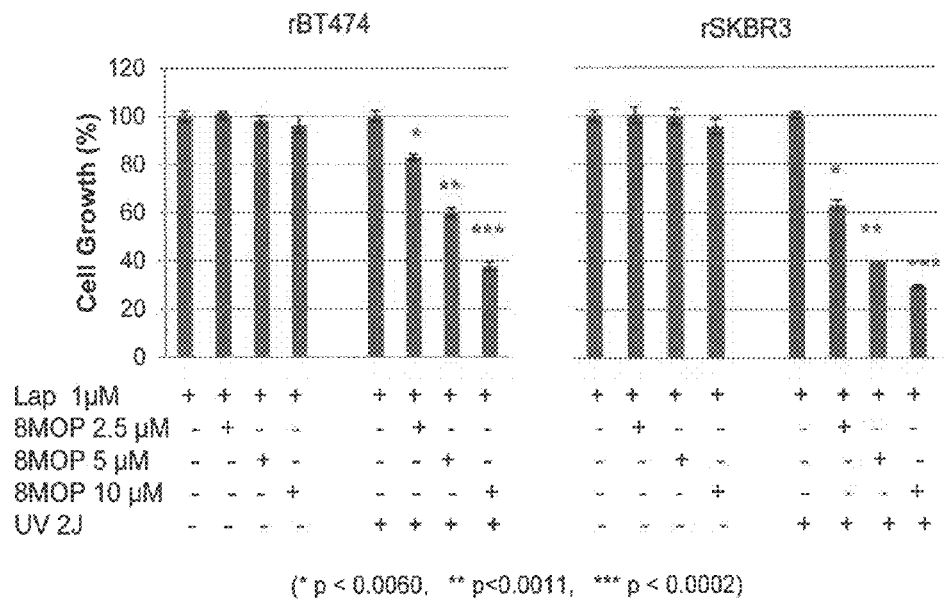
FIG. 6 A-B shows that PUVA therapy reverses acquired resistant to ErbB2 targeted therapies. (A) Equal numbers of rBT474 and rSKBR3 cells were subjected to the indicated treatment conditions, and the effects on cell growth and viability are shown. P values of statistical significance are indicated. Results represent the mean+/−standard error of triplicate samples, and are representative of three independent experiments. (B) The corresponding Western blot analysis for each of the indicated treatment conditions is shown. As indicated, rBT474 and rSKBR3 cells are continuously maintained in 1 µM lapatinib. Actin steady-state protein levels served as a control to ensure for equal loading of protein. Results are representative of three independent experiments.
Figure 6B:
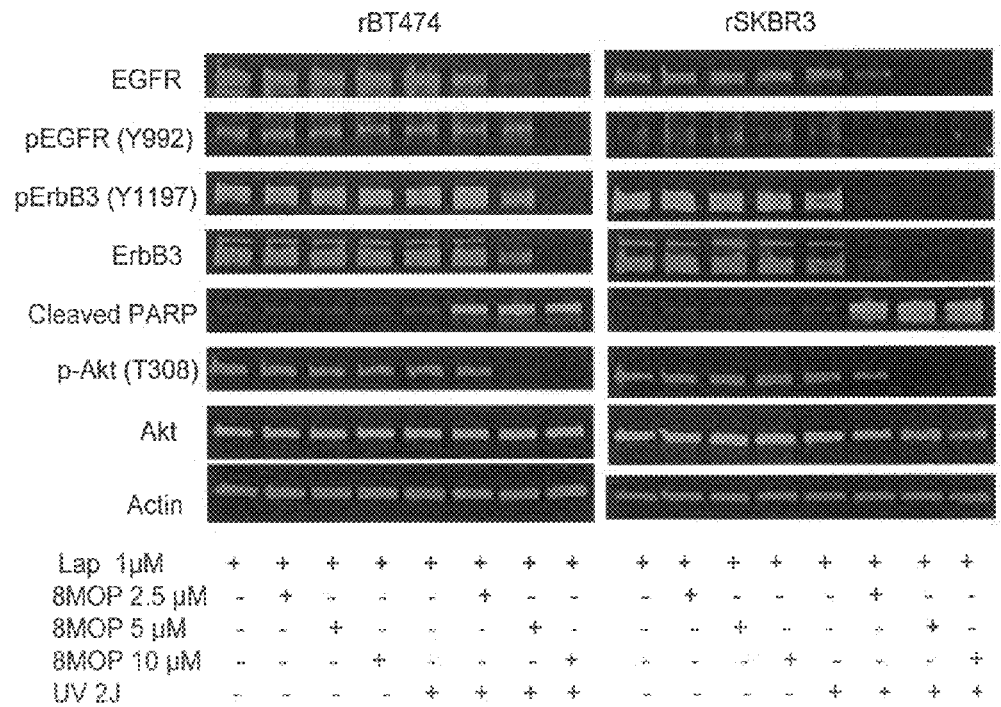

The inventors recently showed that development of acquired therapeutic resistance to the reversible HER2 and EGFR tyrosine kinase inhibitor lapatinib in HER2+ breast cancer cells can be mediated by a number of mechanisms including: (i) a switch in the regulation of cell survival from HER2-HER3-PI3K signaling in treatment naïve cells to EGFR-HER3-PI3K in resistant cells [16]; and (ii) expression of a truncated ErbB2 form preferentially expressed in tumor cell nuclei [17]. It was next sought to determine whether PUVA treatment could reverse lapatinib resistance. Using models of lapatinib resistance established in our laboratory [16-18], rBT474 and rSKBR3 cells were treated with PUVA at the indicated concentrations of 8MOP (FIG. 6A). Resistant cells were continuously maintained in the presence of 1 µM lapatinib. As shown, PUVA treatment significantly reduced tumor cell growth and viability in a dose-dependent manner (FIG. 6A). In contrast to isotype-matched parental cells (FIG. 5), total EGFR and ErbB3 protein expression was markedly reduced in PUVA-treated rBT474 and rSKBR3, in addition to reduction in the expression of phosphorylated forms of EGFR (Y992), ErbB3 (Y1197), and Akt (T308) (FIG. 6B). The effects of PUVA on Akt T308 are particularly interesting in light of our recent finding that Akt T308, but not S473, remained persistently phosphorylated in lapatinib resistant cells [16]. Importantly, PARP cleavage product was increased in PUVA-treated lapatinib resistant tumor cells consistent with induction of apoptosis.

Figure 7:
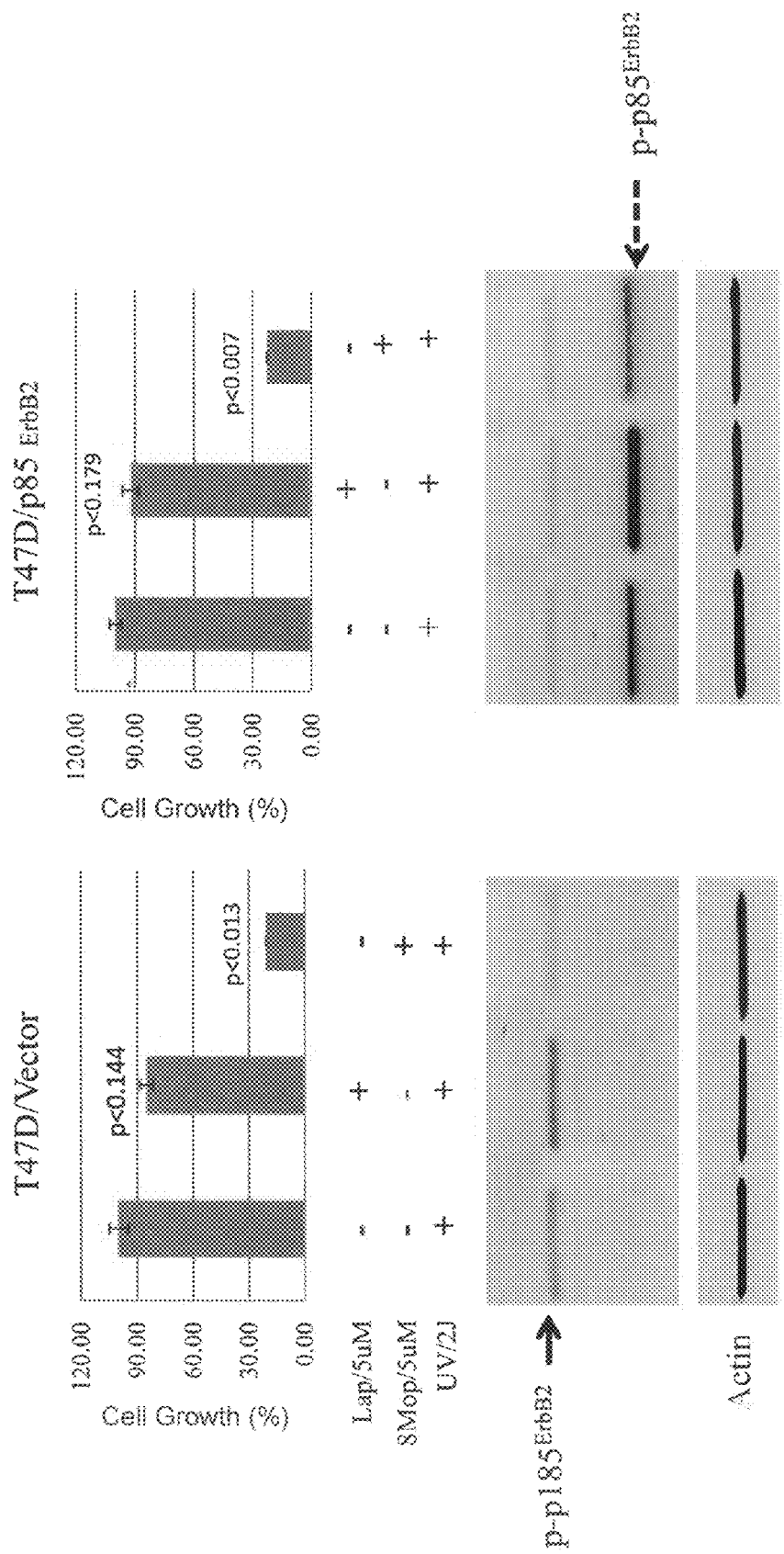
FIG. 7 PUVA therapy targets nuclear $p85^{ErbB2}$, inducing tumor cell apoptosis. Top bar graph shows the results of the growth assays performed in T47D and stably transfected T47D cell line. T47D cells expressing $p85^{ErbB2}$ were pretreated with 5 µM lapatinib or 5 µM 8MOP for 4 hr followed by irradiation in a UV Stratalinker 1800 (Statagene). Cells transfected with empty vector (T47D/Vector), and those treated with vehicle alone (0.01% DMSO) served as controls. The effects of the treatments on cell growth and viability are shown in the bar graph. $P<0.0071$ (8MOP+ UVA irradiation). Results represent the mean+/−standard error of triplicate samples, and are representative of three independent experiments. Steady-state phospho-$p85^{ErbB2}$ protein levels (dotted arrow) and phospho-$p185^{ErbB2}$ (solid arrow) are shown by Western blot. Actin steady-state protein levels served as a control to ensure for equal loading of protein. Results are representative of three independent experiments.

The inventors have also shown that expression of an 85 kDa truncated form of ErbB2 (p85$^{ErbB2}$) that lacks the extracellular and transmembrane domains, is preferentially expressed in the nuclei of tumors that have become resistant to lapatinib [17]. Moreover, expression of p85$^{ErbB2}$ under the control of a heterologous promoter can render cells resistant to lapatinib and other ErbB2 targeted drugs in otherwise sensitive ErbB2+ breast cancer cells [17]. Although p85$^{ErbB2}$ is tyrosine phosphorylation, an indication of its activated state, it is not inhibited by lapatinib (FIG. 7) [17]. To study the effects of PUVA on p85$^{ErbB2}$, the inventors established a T47D transfected breast cancer cell that stably expresses phosphorylated p85$^{ErbB2}$ in tumor cell nuclei as previously described [17]. T47D cells, although not HER2 overexpressing, still express full-length HER2 (FIG. 7). PUVA therapy has an antitumor effect in T47D cells transfected with empty vector alone that is associated full-length ErbB2 (p185$^{ErbB2}$). However, in p85 expressing T47D cells, treatment with PUVA, but not lapatinib, markedly inhibited p85$^{ErbB2}$ phosphorylation, triggering tumor cell apoptosis (FIG. 7).

Obviously, additional modifications and variations of the present invention are possible in light of the above teachings. It is therefore to be understood that within the scope of the appended claims, the invention may be practiced otherwise than as specifically described herein.

REFERENCES

1. Hearst J E, Isaacs S T, Kanne D, Rapoport H, Straub K (1984) The reaction of the psoralens with deoxyribonucleic acid. Q Rev Biophys 17:1-44.
2. Cimino G D, Gamper H B, Isaacs S T, Hearst J E (1985) Psoralens as photoactive probes of nucleic acid structure and function: organic chemistry, photochemistry, and biochemistry. Annu Rev Biochem 54: 1151-1193.
3. Parrish J A, Fitzpatrick T B, Tanenbaum L, Pathak M A (1974) Photochemotherapy of psoriasis with oral methoxsalen and longwave ultraviolet light. N Engl J Med 291: 1207-1211.
4. Berger C L, Cantor C, Welsh J, Dervan P, Begley T, et al. (1985) Comparison of synthetic psoralen derivatives and 8-MOP in the inhibition of lymphocyte proliferation. Ann N Y Acad Sci 453: 80-90.
5. Edelson R L, Berger C, Gasparro F, Jegasothy B, Heald P, et al. (1987) Treatment of cutaneous T cell lymphoma by extracorporeal photochemotherapy. Preliminary results. N Engl J Med 316: 297-303.
6. Greinix H T, Volc-Platzer B, Rabitsch W, Gmeinhart B, Guevara-Pineda C, et al. (1998) Successful use of extracorporeal photochemotherapy in the treatment of severe acute and chronic graft-versus-host disease. Blood 92: 3098-3104.
7. Laskin J D, Lee E, Yurkow E J, Laskin D L, Gallo M A (1985) A possible mechanism of psoralen phototoxicity not involving direct interaction with DNA. Proc Natl Acad Sci US. 82: 6158-6162.
8. Canton M, Cafieri S, Dallon162. F, Di Lisa F (2002) PUVA-induced apoptosis involves mitochondrial dysfunction caused by the opening of the permeability transition pore. FEBS Letters 522: 168-172.

9. Mermelstein H F, Adidi T F, Laskin J D (1989) Inhibition of epidermal growth factor receptor tyrosine kinase activity in A431 human epidermoid cells following psoralen/ultraviolet light treatment. Mol Pharmacology 36: 848-855.
10. Slamon D J, Clark G M, Wong S G, Levin W J, Ullrich A, McGuire W L (1987) Human breast cancer: correlation of relapse and survival with amplification of the HER-2/neu oncogene. Science 235: 177-182.
11. Slamon D J, Godolphin W, Jones L A, Holt J A, Wong S G, et al. (1989) Studies of the HER-2/neu proto-oncogene in human breast and ovarian cancer. Science 244: 707-712.
12. Di Cosimo S, Baselga J (2010) Management of breast cancer with targeted agents: importance of heterogeneity. Nat Rev Clin Oncol 7: 139-147.
13. Geyer C E, Forster J, Lindquist D, Chan S, Romieu C G, et al. (2006) Lapatinib plus capecitabine for HER2-positive advanced breast cancer. N Engl J Med 355: 2733-2743.
14. Johnston S, Trudeau M, Kaufman B, Boussen H, Blackwell K, et al. (2008) Targeting HER2 in advanced inflammatory breast cancer with lapatinib monotherapy: A phase II study with biomarker profiles that predict for response. J Clin Oncol 26: 1066-1072.
15. Nahta R, Yu D, Hung M C, Hortobagyi G N, Esteva F J (2006) Mechanisms of disease: understanding resistance to HER2-targeted therapy in human breast cancer. Nat Clin Pract Oncol 3: 269-280.
16. Xia W, Petricoin E F, Zhao Z, Liu L, Osada T, et al. (2013) An heregulin-EGFR-HER3 autocrine signaling axis can mediate acquired lapatinib resistance in HER2+ breast cancer models. Breast Cancer Res 15: R85.
17. Xia W, Liu Z, Zong R, Liu L, Zhao S, et al. (2011) Truncated ErbB2 Expressed in Tumor Cell Nuclei Contributes to Acquired Therapeutic Resistance to ErbB2 Kinase Inhibitors. Mol Cancer Ther 10: 1367-1374.
18. Xia W, Bacus S, Hegde P, Husain I, Strum J, et al. (2006) A model of acquired autoresistance to ErbB2 tyrosine kinase inhibitors and a therapeutic strategy to prevent its onset in breast cancer. Proc Natl Acad Sci USA 103: 7795-7800.
19. Rabindran S K, Discafani C M, Rosfjord E C, Baxter M, Floyd M B, et al. (2004) Antitumor activity of HKI-272, an orally active, irreversible inhibitor of the HER-2 tyrosine kinase. Cancer Res 264: 3958-3965.
20. Anido J, Scaltriti M, Bech Serra J J, Santiago Josefat B, et al. (2006) Biosynthesis of tumorigenic HER2 C-terminal fragments by alternative initiation of translation. EMBO J 25: 3234-3244.
21. Polier S, Samant R S, Clarke P A, Workman P, Prodromou C, Pearl L H (2013) ATP-competitive inhibitors block protein kinase recruitment to the Hsp90-Cdc37 system. Nat Chem Biol 9: 307-312.
22. Aertgeerts C, Skene R, Yano J, Sang C B, Zou H, et al. (2011) Structural Analysis of the Mechanism of Inhibition and Allosteric Activation of the Kinase Domain of HER2 Protein. J Biol Chem 286: 18756-18765.
23. Xia W, Gerard C M, Liu L, Baudson M N, Ory T L, Spector N L (2005) Combining lapatinib (GW572016), a small molecule inhibitor of ErbB1 and ErbB2 tyrosine kinases, with therapeutic anti-ErbB2 antibodies enhances apoptosis of ErbB2 overexpressing breast cancer cells. Oncogene 24: 6213-6221.
24. Toyooka T and Ibuki Y (2009) Histone Deacetylase Inhibitor Sodium Butyrate Enhances the Cell Killing Effect of Psoralen plus UVA by Attenuating Nucleotide Excision Repair. Cancer Res 69: 3492-3500.
25. Lang K, Lu Y, Jin W, Ang K K, Milas L, Fan Z (2003) Sensitization of breast cancer cells to radiation by trastuzumab. Mol Cancer Ther 2: 1113-1120.

The invention claimed is:
1. A method of inhibition of ErbB2 signaling in cancer cells comprising applying a psoralen derivative lacking a DNA cross-linking motif to cancer cells and applying initiation radiation energy form an energy source, thereby blocking the ErbB2 signaling,
    wherein the psoralen derivative lacking a DNA cross-linking motif is represented by the formula (1):

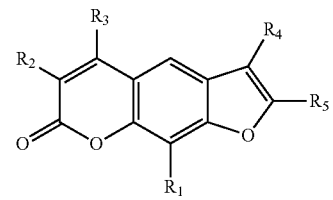

wherein $R_1$ is hydrogen, lower alkyl, or lower alkoxy;
$R_2$ and $R_3$ are each, independently, hydrogen, $C_1$-$C_6$ alkyl, or $C_1$-$C_6$ alkoxy, or $R_2$ and $R_3$ may join to form a substituted or unsubstituted, condensed 5 to 7 membered aliphatic or aromatic ring, optionally containing at least one heteroatom selected from N, S, and O;
$R_4$ and $R_5$ are each, independently, hydrogen, $C_1$-$C_6$ alkyl, or $C_1$-$C_6$ alkoxy, or $R_4$ and $R_5$ may join to form a substituted or unsubstituted, condensed 5 to 7 membered aliphatic or aromatic ring, optionally containing at least one heteroatom selected from N, S, and O;
with the proviso that at least one of $R_2$ and $R_3$ or $R_4$ and $R_5$ are joined to form a substituted or unsubstituted, condensed 5 to 7 membered aliphatic or aromatic ring, optionally containing at least one heteroatom selected from N, S, and O.

2. The method of claim 1, wherein the cancer cells are ErbB2+ breast cancer cells.
3. The method of claim 1, which comprising, prior to said applying the initiation energy, administering to the subject at least one energy modulation agent that converts the initiation energy to an energy that activates the psoralen derivative.
4. The method of claim 1, wherein the at least one energy modulation agent is one or more selected from the group consisting of a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.
5. A method of treating a cell proliferation disorder or disease comprising administering a psoralen derivative lacking a DNA cross-linking motif to a subject in need thereof and applying initiation radiation energy form an energy source,
    wherein the treatment is caused by inducing apoptosis in diseased cells, thereby blocking ErbB2 signaling in cancer cells, wherein the psoralen derivative lacking a DNA cross-linking motif is represented by the formula (1):

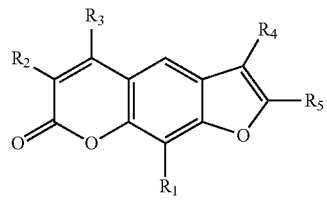

wherein $R_1$ is hydrogen, lower alkyl, or lower alkoxy,
$R_2$ and $R_3$ are each, independently, hydrogen, $C_1$-$C_6$ alkyl, or $C_1$-$C_6$ alkoxy, or $R_2$ and $R_3$ may join to form a substituted or unsubstituted, condensed 5 to 7 membered aliphatic or aromatic ring, optionally containing at least one heteroatom selected from N, S, and O;
$R_4$ and $R_5$ are each, independently, hydrogen, $C_1$-$C_6$ alkyl, or $C_1$-$C_6$ alkoxy, or $R_4$ and $R_5$ may join to form a substituted or unsubstituted, condensed 5 to 7 membered aliphatic or aromatic ring, optionally containing at least one heteroatom selected from N, S, and O;
with the proviso that at least one of $R_2$ and $R_3$ or $R_4$ and $R_5$ are joined to form a substituted or unsubstituted, condensed 5 to 7 membered aliphatic or aromatic ring, optionally containing at least one heteroatom selected from N, S, and O.

6. The method of claim 5, wherein the diseased cells are ErbB2+ breast cancer cells.

7. The method of claim 1 or 5, wherein the initiation radiation energy is UVA or visible energy.

8. The method of claim 1 or 5, wherein the initiation radiation energy is applied via a thin fiber optic.

9. The method of claim 1 or 5, wherein the psoralen derivative is SMSF032310.

10. The method of claim 5, wherein the cell proliferation disorder or disease is cancer.

11. The method of claim 10, wherein the cell proliferation disorder or disease is breast cancer.

12. The method of claim 5, which comprising, prior to said applying the initiation energy, administering to the subject at least one energy modulation agent that converts the initiation energy to an energy that activates the psoralen derivative.

13. The method of claim 5, wherein the at least one energy modulation agent is one or more selected from the group consisting of a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

14. A method of treating a cell proliferation disorder or disease comprising administering a psoralen or substituted psoralen and lapatinib to a subject in need thereof and applying initiation radiation energy form an energy source,
wherein the treatment reduces diseased cell growth and/or viability compared to that of diseased cells treated with lapatinib alone, or a combination of lapatinib and the psoralen or psoralen derivative, or a combination of lapatinib and the initiation radiation energy.

15. The method of claim 14, wherein the treatment reduces tumor cell growth and/or viability in lapatinib resistant tumor cells.

16. The method of claim 15, wherein the lapatinib resistant tumor cells are HER2+ breast cancer cells.

17. The method of claim 14, wherein the initiation radiation energy is UVA or visible energy.

18. The method of claim 14, wherein the psoralen or substituted psoralen is 8-Methoxypsoralen (8-MOP), 4'-aminomethyl-4,5',8-trimethylpsoralen (AMT), or SMSF032310.

19. The method of claim 14, wherein the cell proliferation disorder or disease is breast cancer.

20. The method of claim 14, which comprising, prior to said applying the initiation energy, administering to the subject at least one energy modulation agent that converts the initiation energy to an energy that activates the psoralen derivative.

21. The method of claim 15, wherein the at least one energy modulation agent is one or more selected from a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

22. A method of treating a cell proliferation disorder or disease comprising administering a psoralen or substituted psoralen and neratinib to a subject in need thereof and applying initiation radiation energy form an energy source,
wherein the treatment reduces diseased cell growth and/or viability compared to that of diseased cells treated with neratinib alone, or a combination of neratinib and the psoralen or psoralen derivative, or a combination of neratinib and the radiation energy.

23. The method of claim 22, wherein the diseased cells are tumor cells.

24. The method of claim 23, wherein the tumor cells are ErbB2+ breast cancer cells.

25. The method of claim 22, wherein the radiation energy is UVA or visible energy.

26. The method of claim 22, wherein the psoralen or substituted psoralen is 8-Methoxypsoralen (8-MOP), 4'-aminomethyl-4,5',8-trimethylpsoralen (AMT), or SMSF032310.

27. The method of claim 22, wherein the cell proliferation disorder or disease is breast cancer.

28. The method of claim 22, which comprising, prior to said applying the initiation energy, administering to the subject at least one energy modulation agent that converts the initiation energy to an energy that activates the psoralen derivative.

29. The method of claim 22, wherein the at least one energy modulation agent is one or more selected from the group consisting of a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

* * * * *